US012633401B2

(12) United States Patent
Rush et al.

(10) Patent No.: US 12,633,401 B2
(45) Date of Patent: May 19, 2026

(54) MODULAR AUTOMATED PHYSICAL HEALTH TESTING SYSTEMS AND ASSOCIATED DEVICES AND METHODS

(71) Applicant: Reperio Health, Inc., Portland, OR (US)

(72) Inventors: Travis Benjamin Rush, Happy Valley, OR (US); Matthew Robert Wallington, Oregon City, OR (US)

(73) Assignee: Reperio Health, Inc., Portland, OR (US)

( * ) Notice: Subject to any disclaimer, the term of this patent is extended or adjusted under 35 U.S.C. 154(b) by 138 days.

(21) Appl. No.: 18/361,711

(22) Filed: Jul. 28, 2023

(65) Prior Publication Data

US 2023/0377733 A1 Nov. 23, 2023

Related U.S. Application Data

(63) Continuation of application No. 17/961,552, filed on Oct. 6, 2022, now Pat. No. 11,763,938, which is a
(Continued)

(51) Int. Cl.
*G16H 40/20* (2018.01)
*A61B 3/00* (2006.01)
(Continued)

(52) U.S. Cl.
CPC .......... *G16H 40/20* (2018.01); *A61B 5/0205* (2013.01); *A61B 50/30* (2016.02); *G16H 10/40* (2018.01);
(Continued)

(58) Field of Classification Search
None
See application file for complete search history.

(56) References Cited

U.S. PATENT DOCUMENTS 5,078,134 A 1/1992 Heilman et al.
5,752,234 A 5/1998 Withers
(Continued)

FOREIGN PATENT DOCUMENTS

CN 204207739 A 3/2015
CN 106175751 A 12/2016
WO 2015138515 A1 9/2015

OTHER PUBLICATIONS

European Patent Office, International Search Report and Written Opinion mailed Feb. 17, 2021 for PCT International Application No. PCT/US2020/058163 filed Oct. 30, 2020, 13 pages.
(Continued)

*Primary Examiner* — Benjamin S Melhus
(74) *Attorney, Agent, or Firm* — Perkins Coie LLP

(57) ABSTRACT

Automated modular physical health testing systems and associated devices and methods are disclosed herein. A modular system configured in accordance with embodiments of the present technology can include, for example, a housing, a communications hub, and a plurality of physical health testing devices. The housing integrates the communications hub and stores the plurality of physical health testing devices. The physical health testing devices are in wired and/or wireless communication with the communications hub. Each physical health testing device is configured to generate physical health data of a user and to transmit generated physical health data to the communication hub and/or a user's mobile device. The modular physical health testing system provides an automated physical exam that can be performed at user's homes or other convenient locations.

21 Claims, 15 Drawing Sheets

Related U.S. Application Data continuation of application No. 17/085,293, filed on Oct. 30, 2020, now Pat. No. 11,488,707.

(60) Provisional application No. 62/928,146, filed on Oct. 30, 2019.

(51) Int. Cl.

| | |
|---|---|
| *A61B 5/00* | (2006.01) |
| *A61B 5/01* | (2006.01) |
| *A61B 5/0205* | (2006.01) |
| *A61B 5/022* | (2006.01) |
| *A61B 5/024* | (2006.01) |
| *A61B 5/107* | (2006.01) |
| *A61B 5/145* | (2006.01) |
| *A61B 5/15* | (2006.01) |
| *A61B 5/151* | (2006.01) |
| *A61B 5/332* | (2021.01) |
| *A61B 7/04* | (2006.01) |
| *A61B 50/30* | (2016.01) |
| *A61B 50/36* | (2016.01) |
| *A61F 17/00* | (2006.01) |
| *G06Q 50/26* | (2024.01) |
| *G16H 10/40* | (2018.01) |
| *G16H 10/60* | (2018.01) |
| *G16H 15/00* | (2018.01) |
| *G16H 40/67* | (2018.01) |
| *G16H 50/20* | (2018.01) |
| *G16H 50/30* | (2018.01) |
| *G16H 50/70* | (2018.01) |
| *G16H 70/20* | (2018.01) |

(52) U.S. Cl.

CPC ............. *G16H 10/60* (2018.01); *G16H 15/00* (2018.01); *G16H 40/67* (2018.01); *G16H 50/20* (2018.01); *G16H 50/30* (2018.01); *G16H 50/70* (2018.01); *G16H 70/20* (2018.01); *A61B 3/00* (2013.01); *A61B 5/002* (2013.01); *A61B 5/01* (2013.01); *A61B 5/022* (2013.01); *A61B 5/02438* (2013.01); *A61B 5/1072* (2013.01); *A61B 5/14532* (2013.01); *A61B 5/14546* (2013.01); *A61B 5/150305* (2013.01); *A61B 5/151* (2013.01); *A61B 5/332* (2021.01); *A61B 7/04* (2013.01); *A61B 2050/3008* (2016.02); *A61B 2050/3014* (2016.02); *A61B 50/36* (2016.02); *A61B 2560/0431* (2013.01); *A61F 17/00* (2013.01); *G06Q 50/26* (2013.01)

(56) References Cited

U.S. PATENT DOCUMENTS

| | | | |
|---|---|---|---|
| 6,047,203 | A | 4/2000 | Sackner et al. |
| 7,395,106 | B2 | 7/2008 | Ryu et al. |
| 7,673,952 | B2 | 3/2010 | Brown |
| 8,353,827 | B2 | 1/2013 | Brown |
| 9,282,893 | B2 | 3/2016 | Longinotti-Buitoni et al. |
| 10,085,517 | B2 | 10/2018 | Beers et al. |
| 11,017,116 | B2 | 5/2021 | Riddle et al. |
| 11,488,707 | B2 | 11/2022 | Rush et al. |
| 11,763,938 | B2 | 9/2023 | Rush et al. |
| 2002/0115912 | A1 | 8/2002 | Muraki et al. |
| 2003/0069752 | A1 | 4/2003 | LeDain et al. |
| 2008/0221404 | A1 | 9/2008 | Tso |
| 2009/0240528 | A1 | 9/2009 | Bluth |
| 2012/0136231 | A1 | 5/2012 | Markel |
| 2013/0023741 | A1 | 1/2013 | Ayanruoh |
| 2013/0125158 | A1 | 5/2013 | Brown |
| 2014/0018879 | A1 | 1/2014 | Worrell et al. |
| 2014/0058755 | A1 | 2/2014 | Macoviak et al. |
| 2014/0122115 | A1 | 5/2014 | Bagan |
| 2014/0135593 | A1 | 5/2014 | Jayalth et al. |
| 2014/0206977 | A1 | 7/2014 | Bahney et al. |
| 2014/0263346 | A1 | 9/2014 | Bowen et al. |
| 2014/0330579 | A1 | 11/2014 | Cashman et al. |
| 2015/0045632 | A1 | 2/2015 | Bagan |
| 2015/0107377 | A1 | 4/2015 | Bagan |
| 2015/0335288 | A1 | 11/2015 | Toth et al. |
| 2015/0350861 | A1 | 12/2015 | Soli et al. |
| 2016/0346056 | A1 | 12/2016 | Demers et al. |
| 2017/0258995 | A1 | 9/2017 | Hyde et al. |
| 2018/0114601 | A1 | 4/2018 | Ou et al. |
| 2020/0078127 | A1 | 3/2020 | Demers et al. |
| 2020/0098461 | A1 | 3/2020 | Macoviak et al. |
| 2023/0036307 | A1 | 2/2023 | Rush et al. |
| 2023/0172544 | A1 | 6/2023 | Rush et al. |

OTHER PUBLICATIONS

ISA/US International Search Report and Written Opinion mailed Aug. 16, 2021 for PCT International patent application No. PCT/US21/30330 filed Apr. 30, 2021, 9 pages.

FDA.gov, Webpage Archive, https://web.archive.org/web/20191017162927/https://www.fda.gov/news-events/approvals-fda-regulated-products/about-fda-product-approval , Year: 2019.

Australian Examination Report for Australian patent application No. 2020375934, issued Aug. 23, 2024, Applicant: Reperio Health, Inc., 3 pages.

Canadian Examination Report for Canadian patent application No. 3159760, issued Jan. 28, 2025, Applicant: Reperio Health, Inc., 3 pages.

Extended European Search Report for European patent application No. 21796872.6, issued Mar. 7, 2024, Applicant: Reperio Health, Inc., 8 pages.

Acceptance Notice issued for South African patent application 2022/05290 on Nov. 1, 2023, Applicant: Reperio Health, Inc.

USPTO Office Action mailed Feb. 25, 2025 for U.S. Appl. No. 17/922,343, First Named Inventor: Travis Benjamin Rush, 20 pages.

Notice of Acceptance for Australian patent application No. 2020375934, issued Jun. 11, 2025, Applicant: Reperio Health, Inc., 3 pages.

Examination Report for European patent application No. 20812474.3, issued May 9, 2025, Applicant: Reperio Health, Inc., 7 pages.

CNIPA Examination Report for Application No. 202211037099.3, issued Jun. 27, 2025, 4 pages.

| Receiver 215a |
| Transmitter 215b |
| Controller/Processor 215c |

881    882    883    880

99.3367 kg

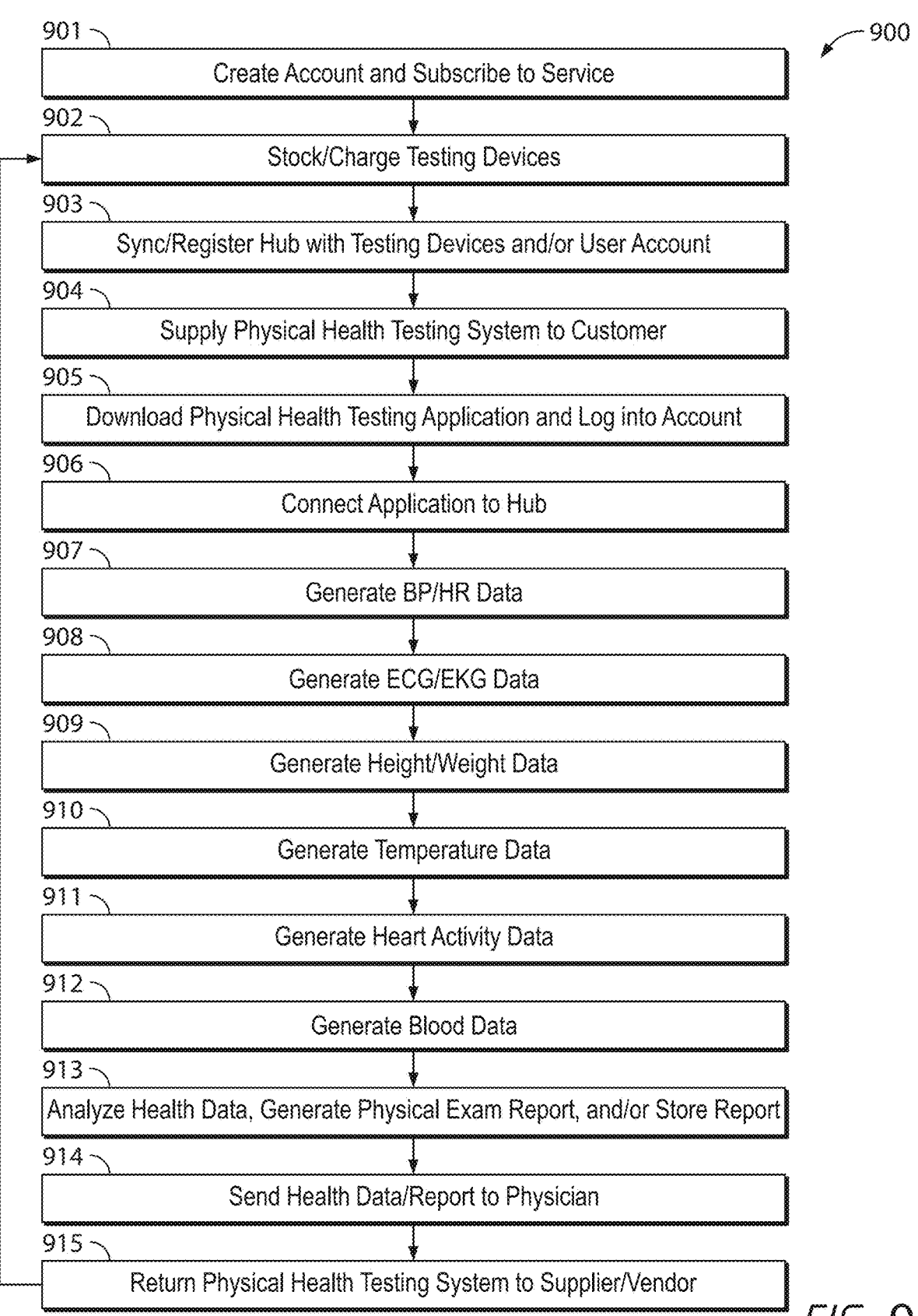

901 — Create Account and Subscribe to Service

902 — Stock/Charge Testing Devices

903 — Sync/Register Hub with Testing Devices and/or User Account

904 — Supply Physical Health Testing System to Customer

905 — Download Physical Health Testing Application and Log into Account

906 — Connect Application to Hub

907 — Generate BP/HR Data

908 — Generate ECG/EKG Data

909 — Generate Height/Weight Data

910 — Generate Temperature Data

911 — Generate Heart Activity Data

912 — Generate Blood Data

913 — Analyze Health Data, Generate Physical Exam Report, and/or Store Report

914 — Send Health Data/Report to Physician

915 — Return Physical Health Testing System to Supplier/Vendor

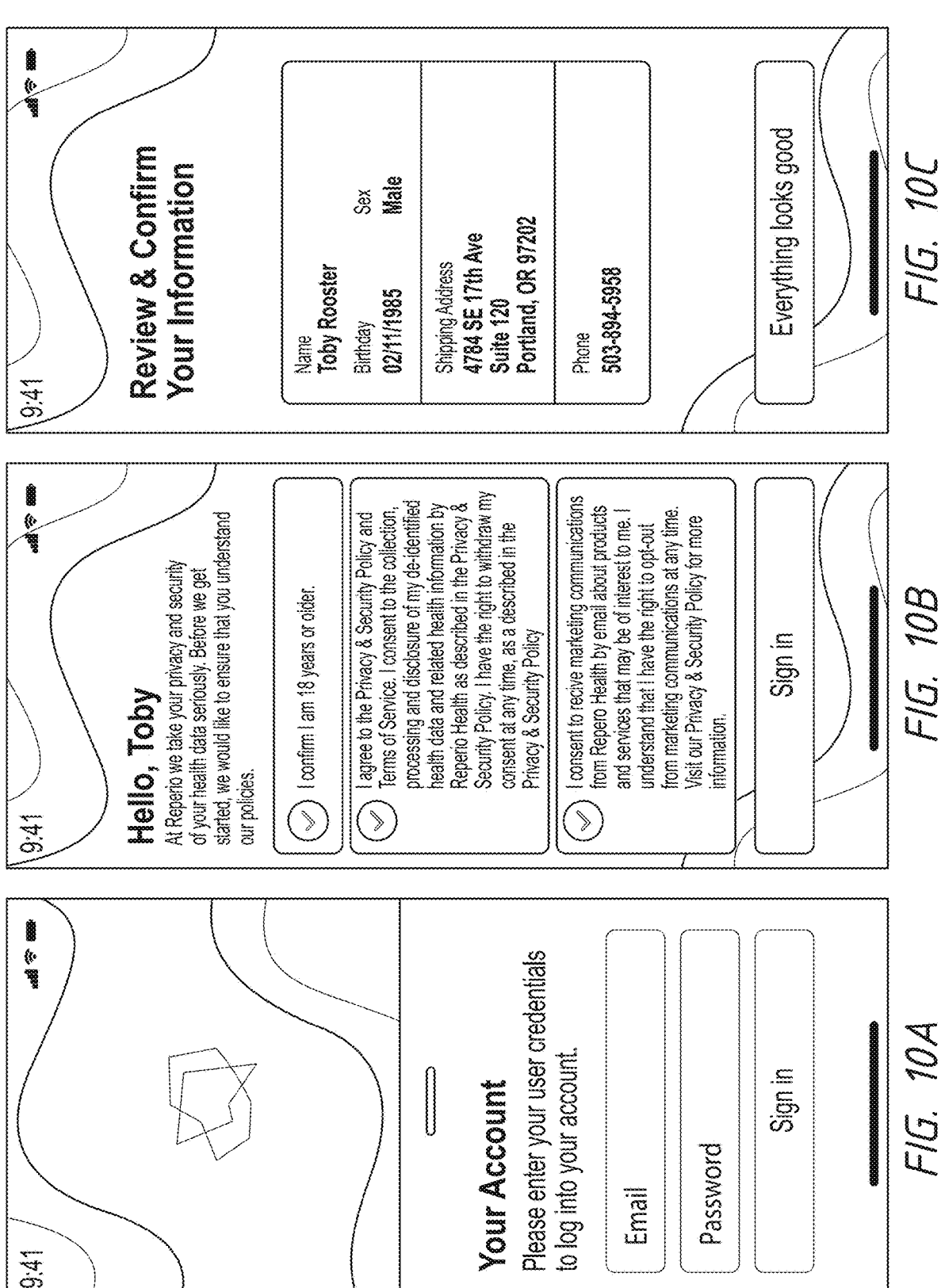

Your Account

Please enter your user credentials to log into your account.

Email

Password

Sign in

*FIG. 10A*

Hello, Toby

At Reperio we take your privacy and security of your health data seriously. Before we get started, we would like to ensure that you understand our policies.

> I confirm I am 18 years or older.

> I agree to the Privacy & Security Policy and Terms of Service. I consent to the collection, processing and disclosure of my de-identified health data and related health information by Reperio Health as described in the Privacy & Security Policy. I have the right to withdraw my consent at any time, as a described in the Privacy & Security Policy > I consent to recive marketing communications from Reperio Health by email about products and services that may be of interest to me. I understand that I have the right to opt-out from marketing communications at any time. Visit our Privacy & Security Policy for more information.

Sign in

*FIG. 10B*

Review & Confirm Your Information

Name
Toby Rooster

Birthday                Sex
02/11/1985          Male

Shipping Address
4784 SE 17th Ave
Suite 120
Portland, OR 97202

Phone
503-894-5958

Everything looks good

*FIG. 10C*

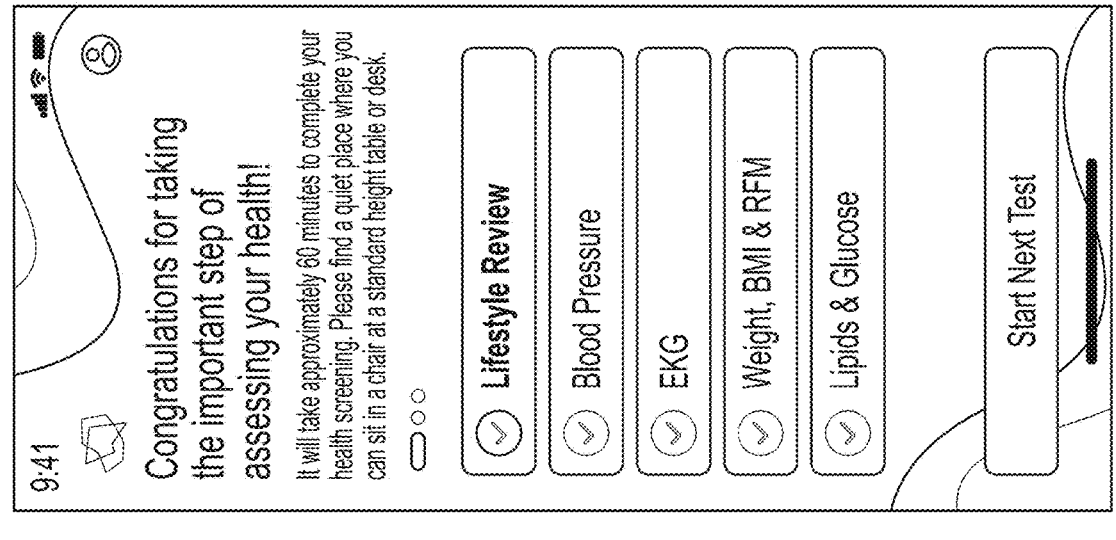

9:41

We have a few questions about your health care.

Please complete the question below. You can always update your answer later

> Do you have a Primary Care Physician?
> Yes

> Do you have health insurance?
> Individual plan

> Why did you decide to try Reperio?
> Haven't had a recent physical

Next

*FIG. 10D*

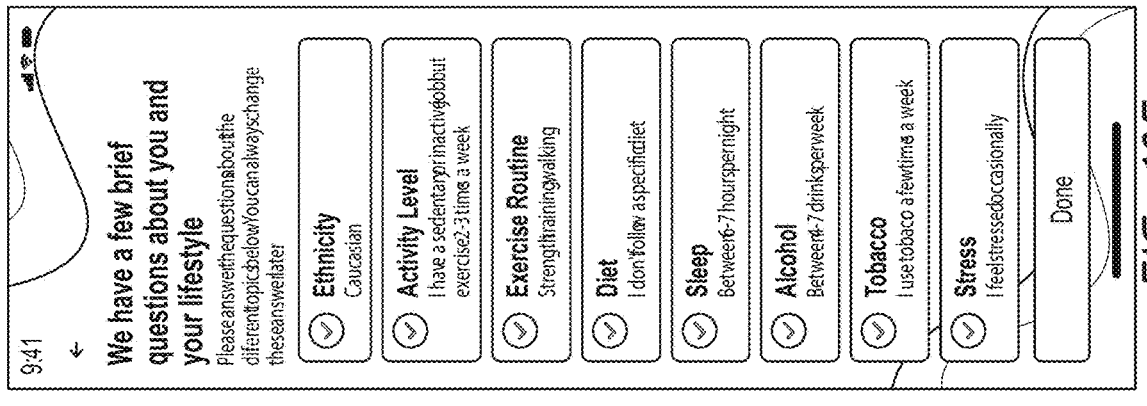

9:41

We have a few brief questions about you and your lifestyle

Please answer the question about the different topic below. You can always change these answer later > Ethnicity
> Caucasian > Activity Level
> I have a sedentary or inactive job but I exercise 2-3 time a week > Exercise Routine
> Strength training, walking > Diet
> I don't follow a specific diet > Sleep
> Between 6-7 hours per night > Alcohol
> Between 4-7 drinks per week > Tobacco
> I use tobacco a few time a week > Stress
> I feel stressed occasionally Done

*FIG. 10E*

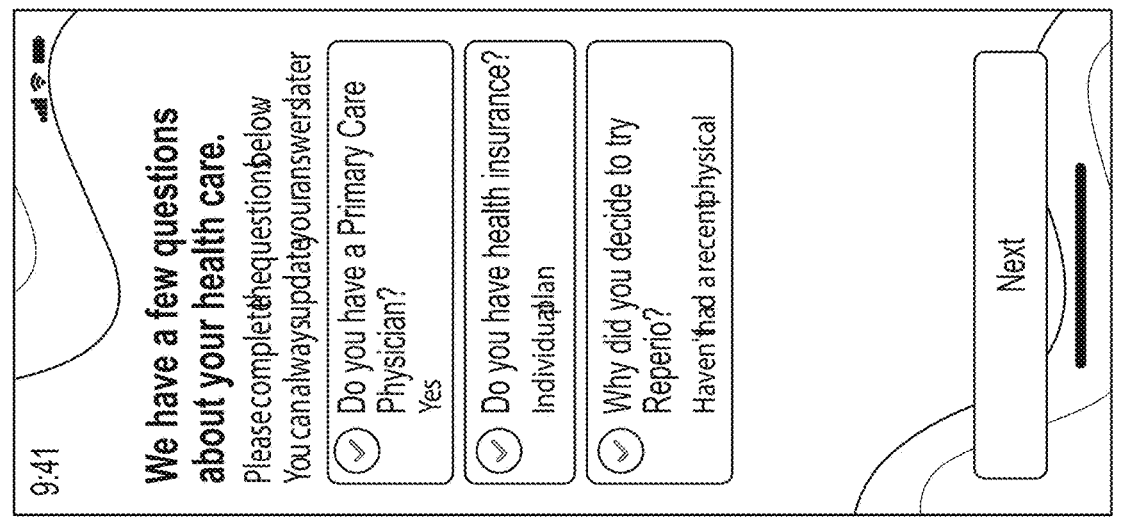

9:41

Congratulations for taking the important step of assessing your health!

It will take approximately 60 minutes to complete your health screening. Please find a quiet place where you can sit in a chair at a standard height table or desk.

> Lifestyle Review

> Blood Pressure

> EKG

> Weight, BMI & RFM

> Lipids & Glucose

Start Next Test

*FIG. 10F*

MODULAR AUTOMATED PHYSICAL HEALTH TESTING SYSTEMS AND ASSOCIATED DEVICES AND METHODS

CROSS-REFERENCE TO RELATED APPLICATIONS

This application is a continuation of U.S. patent application Ser. No. 17/961,552 filed Oct. 6, 2022, which is a continuation of U.S. patent application Ser. No. 17/085,293 filed Oct. 30, 2020, now issued as U.S. Pat. No. 11,488,707, which claims the benefit of U.S. Provisional Patent Application No. 62/928,146, filed Oct. 30, 2019, all of which are incorporated by reference herein in their entirety.

TECHNICAL FIELD

The present disclosure relates generally to systems for providing physical health screening exams. More specifically, the present disclosure relates to modular automated physical health testing systems and associated devices and methods.

BACKGROUND

A physical exam, or "physical," is a screening test that is executed by a healthcare professional, such as a primary care provider, in a medical office to assess a person's overall health. A physical exam evaluates patient vitals and other diagnostic parameters to detect various medical conditions, identify potential medical issues that may be of concern in the future, track changes in a person's physical health over time, and/or determine whether an individual requires further medical tests. As such, routine physical exams (e.g., once or twice per year) are essential for tracking an individual's medical history and detecting potential health concerns in early stages.

Despite the clear benefits, many individuals do not undergo routine physical exams for a variety of reasons. These include, among other reasons, travel time to physician's office, inconvenience of scheduling and going to a doctor's appointment, difficulty getting time off work, financial uncertainty of the cost of a hospital visit, and/or low urgency or priority, especially when the individual currently feels fine. Furthermore, physicals are not always prioritized by healthcare providers and systems due to the inherent lack of acuity, the overall needs of medically underserved areas, and/or low reimbursement rates. Delaying or eliminating routine physical exams, however, decreases the likelihood of early diagnosis and intervention, and decreases patient medical history that can be important for diagnosis and treatment when it becomes necessary.

Furthermore, the complexity and high costs associated with portable and/or home-use diagnostic testing equipment is prohibitive for many. Further, the ability to understand the diagnostic test results, identify whether the at-home diagnostic test was performed properly, and accurately aggregate the results of multiple tests in a meaningful manner to provide a picture of their overall health limit the utility of portable, at-home diagnostic tests.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

FIG. 9 is a flow diagram illustrating a physical exam routine using a modular physical health testing system configured in accordance with various embodiments of the present technology.

DETAILED DESCRIPTION

Figure 1:
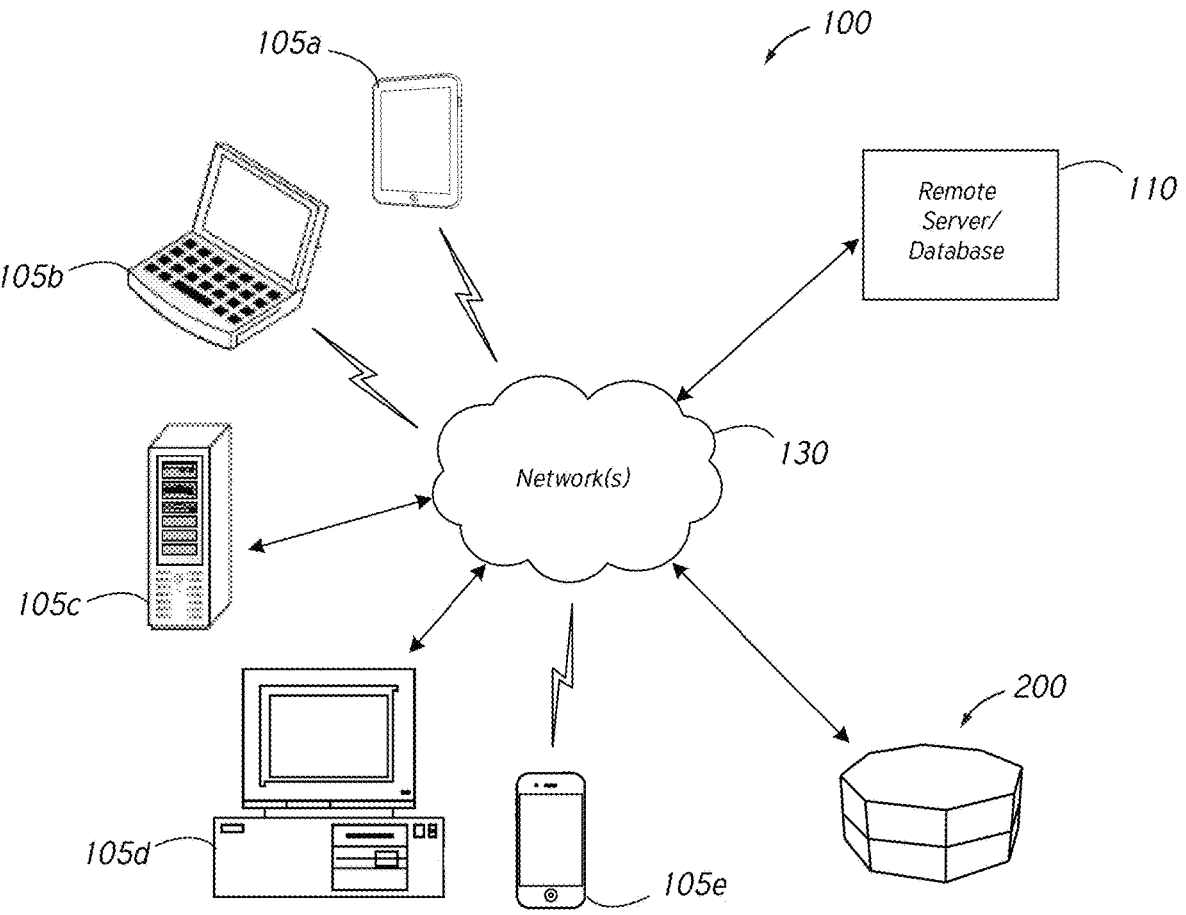
FIG. 1 is a block diagram of an environment for operating a modular physical health testing system in accordance with various embodiments of the present technology.

The following disclosure describes automated modular physical health testing systems, and associated devices and methods. In particular, the following disclosure describes a modular physical health testing system that includes a plurality of physical health testing devices for a user to perform a physical exam on his/her own and/or apart from a healthcare professional. As an example, the present disclosure describes modular systems that integrate a plurality of physical health testing devices and software applications, a communications hub, and a disposal container. This integrated physical exam system can interface with a software application (e.g., a mobile application) on a user device and/or one or more remote servers/databases. In some embodiments, the physical health testing devices include a thermometer, a blood pressure and/or heart rate cuff and/or monitor, an ECG or EKG device, a stethoscope, a glucose and/or cholesterol blood test system, a scale, a tape measure, and/or other physical health testing devices. Using the physical health testing devices, a user performs a variety of physical health tests to generate data related to his/her health that can then be assessed and used by medical professionals and form a part of the patient's medical history.

The physical health testing devices are in wired or wireless communication with the communications hub. In turn, the hub is in wired or wireless communication with the software application running on a user's electronic device, which can provide instructions and interfaces that guide the user through a series of tests provided by the integrated physical exam system. As the plurality of physical health testing devices and/or a user generate health data related to the user, the testing devices and/or the user communicate the health data to the hub, and the hub associates the health data with the user's account and/or stores the health data for future reference/review. Additionally, or alternatively, the testing devices communicate health data to the user via the software application and/or via indicators on a corresponding physical health testing device. In some embodiments, the modular physical health testing system can provide information to the user (e.g., via the mobile application) related to the recorded data, such as whether certain measurements are in a predetermined "healthy" range and/or provide recommendations related to the recorded data that the user consult a healthcare professional (e.g., if the generated health data related to the user is outside of a healthy range of values). In these and other embodiments, a user can send the health data to a healthcare professional via the modular physical health testing system and/or a user device running the software application, and/or can generate a code for the user to share with a healthcare professional who can use the code to retrieve health data generated during the physical exam(s) and corresponding to the user.

Because the physical health testing system already includes a collection of physical health testing devices that can be used to perform a meaningful physical exam, users need not shoulder the time and financial cost required to research and separately purchase each device to conduct a physical exam at home. Additionally, because the communications hub of the physical health testing system handles communication between physical health testing devices of the physical health testing system and the software application on the user's device, the user is not required to download a separate software application for each of the physical health testing devices. Rather, the user can conduct multiple physical health tests using several of the physical health testing devices of the physical health testing system while interfacing with only the single software application on the user's device that is in communication with the communications hub. Furthermore, because the physical health testing system is portable, a user can run a variety of physical health tests from any location (e.g., at home, at work, at a hotel, at an assisted living facility, at a gym, at school) and/or at a time that is convenient for him/her, thereby obviating the practice and inconvenience of scheduling and attending a doctor's appointment for a physical exam. In addition, the physical health testing system can (i) accurately interpret the results of each physical health test a user conducts and (ii) accurately aggregate the results of one or more of the tests together to compile a picture of the user's overall health. Thus, users need not interpret test results on their own. Moreover, because the physical exam can be performed outside of a hospital or medical facility and/or without supervision of a healthcare professional, users can undergo a physical exam without unexpected hospital bills. In addition, the modular physical health testing systems free up healthcare time, funds, and resources to be spent on treating patients with more acute needs. In turn, users are more likely to stay current on their routine physical exams, increasing the chances of early detection of medical concerns and generating a wealth of medical history data for healthcare professionals to consult when a patient does become ill.

Certain details are set forth in the following description and in FIGS. 1-10N to provide a thorough understanding of various embodiments of the disclosure. However, other details describing well-known structures and systems often associated with physical health testing systems and associated methods are not set forth below to avoid unnecessarily obscuring the description of various embodiments of the disclosure.

Many of the details, dimensions, angles, and other features shown in FIGS. 1-9 are merely illustrative of particular embodiments of the disclosure. Accordingly, other embodiments can have other details, dimensions, angles, and features without departing from the spirit or scope of the present disclosure. In addition, those of ordinary skill in the art will appreciate that further embodiments of the disclosure can be practiced without several of the details described below.

A. SELECTED EMBODIMENTS OF MODULAR PHYSICAL HEALTH TESTING SYSTEMS AND ASSOCIATED DEVICES AND METHODS

FIG. 1 is a block diagram of an environment 100 in which a modular physical health testing system 200 ("the modular system 200" or "the system 200") operates, configured in accordance with various embodiments of the present technology. In the environment 100, the system 200 can connect to (e.g., wirelessly and/or via one or more wires) and/or communicate with one or more devices 105 (identified individually as 105a-e in FIG. 1) over one or more networks 130, including public or private networks (e.g., the internet). The one or more devices 105 can include personal computers, server computers, handheld or laptop devices, cellular telephones, wearable electronics, tablet devices, multiprocessor systems, microprocessor-based systems, set-top boxes, programmable consumer electronics, network PCs, minicomputers, mainframe computers, distributed computing environments that include any of the above systems or devices, or the like. In these and other embodiments, the one or more devices 105 can include other remote or local devices, such as landline phones, fax machines, medical devices, thermostats, speakers, and other devices.

As shown in FIG. 1, the system 200 can connect to and/or communicate with one or more remote servers/databases 110 (e.g., directly and/or via one or more of the devices 105, such as user device 105e). In some embodiments, a remote server/database 110 can be an edge server which receives client requests and coordinates fulfillment of those requests through other servers. The remote servers/databases 110 can comprise computing systems. Although the remote servers/databases 110 are displayed logically as a single server/database, the remote servers/databases 110 can be a distributed computing environment encompassing multiple computing devices and/or databases located at the same or at geographically disparate physical locations. In some embodiments, the remote servers/databases 110 correspond to a group of servers.

In some embodiments, the one or more devices 105, the system 200, and/or the remote servers/databases 110 can each act as a server or client to other server/client devices. The remote servers/databases 110 can include one or more databases. The one or more databases can warehouse (e.g. store) information such as health educational lessons, health information, various alerts or warnings, user accounts/profiles, generated health data, drivers/software necessary to operate certain applications and/or devices, and/or other information.

The one or more networks 130 allow for communication in the environment 100. The one or more networks 130 can include one or more wireless networks, such as, but not limited to, one or more of a Local Area Network (LAN), Wireless Local Area Network (WLAN), a Personal Area Network (PAN), Campus Area Network (CAN), a Metropolitan Area Network (MAN), a Wide Area Network (WAN), a Wireless Wide Area Network (WAN), Global System for Mobile Communications (GSM), Personal Communications Service (PCS), Digital Advanced Mobile Phone Service (D-Amps), Bluetooth, Wi-Fi, Fixed Wireless Data, 2G, 2.5G, 3G, 3.75G, 4G, 5G, LTE networks, enhanced data rates for GSM evolution (EDGE), General packet radio service (GPRS), enhanced GPRS, messaging protocols such as, TCP/IP, SMS, MMS, extensible messaging and presence protocol (XMPP), real time messaging protocol (RTMP), instant messaging and presence protocol (IMPP), instant messaging, USSD, IRC, or any other wireless data networks or messaging protocols. Network 130 may also include wired networks.

Figure 2A:
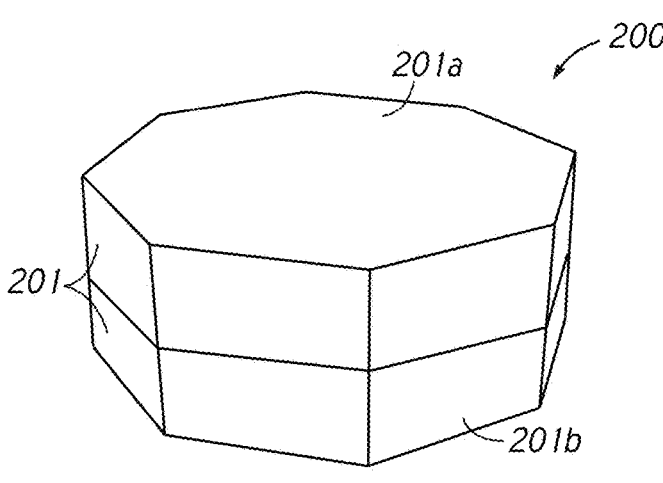
FIG. 2A is a perspective view of an automated modular physical health testing system configured in accordance with various embodiments of the present technology.

FIG. 2A is a perspective view of a modular physical health testing system 200 configured in accordance with various embodiments of the present technology. The system 200 includes a housing 201 having a first portion 201a and a second portion 201b. The housing 201 is illustrated as having an octagonal shape in FIG. 2A, but the housing 201 can have another shape (e.g., triangle, rectangle, square, pentagonal, hexagonal, etc.) in other embodiments. As described in greater detail below with respect to FIGS. 2B-8, the housing 201 is configured to house/store, protect, and/or integrate a plurality of physical health testing devices ("testing devices") and related objects. In some embodiments, the first portion 201a is configured to removably interface (e.g., connect) with the second portion 201b such that the system 200 is sealed and/or water resistant (e.g. protected against vertical water drop) at least at locations where the first portion 201a and the second portion 201b interface with one another. Removal of the first portion 201a may provide access to one or more of the health testing devices, either via an interface exposed by removal of the first portion 201a and/or allowing removal of the health testing devices from the housing 201. In some embodiments, the testing devices may be accessible via one or more exterior surfaces of the housing 201. The first portion 201a and/or the second portion 201b can be made from one or more polymers (e.g., one or more plastics or resins) or other suitable materials such that the housing 201 is chemical-resistant and/or provides the system 200 impact durability. In some embodiments, the housing 201 can have a box-like structure and can be shaped and sized such that it is large enough to house the plurality of physical health testing devices and related objects but small enough to remain portable (e.g., to conveniently ship (e.g., to a user) with parcel shipping and/or move around a user's home after arrival). For example, the housing 201 can be approximately 370 mm (e.g., 150 mm to 610 mm, such as 300 mm to 450 mm, or about 380 mm) in length, approximately 370 mm (e.g., 150 mm to 610 mm, such as 300 mm to 450 mm, or about 380 mm) in width, and approximately 115 mm (e.g., 40 mm to 215 mm, such as 75 mm to 175 mm, or about 130 mm) in height.

Figure 2B:
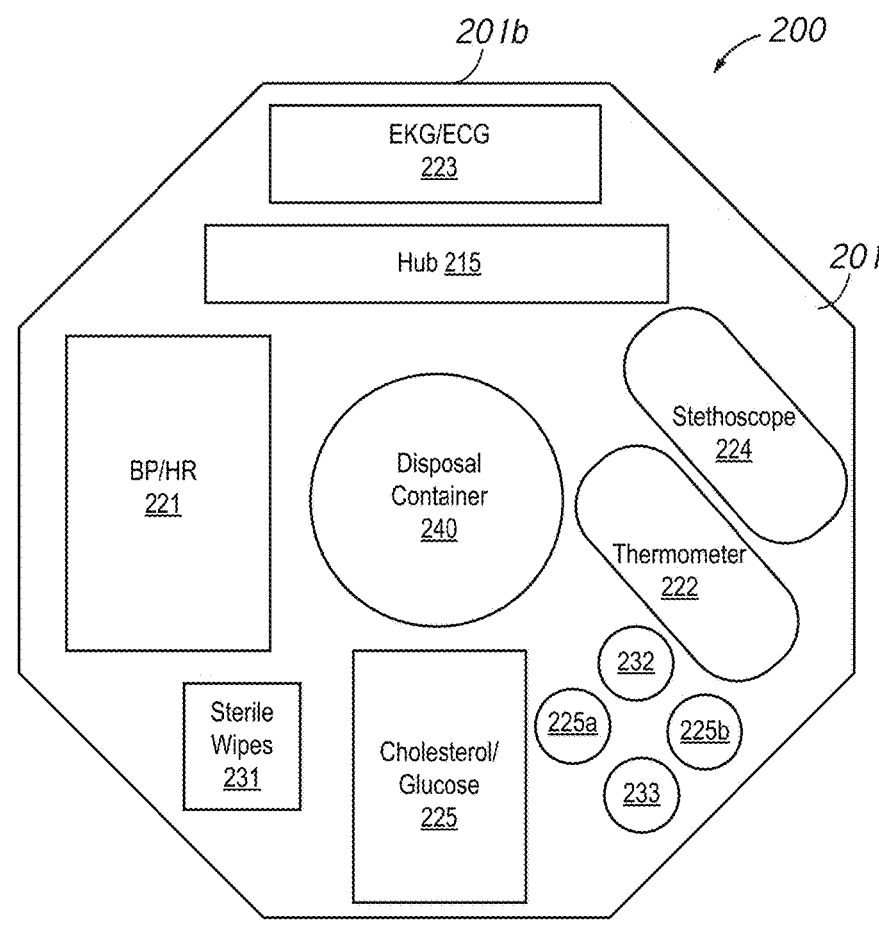
FIG. 2B is a partially schematic top view of the modular physical health testing system of FIG. 2A configured in accordance with some embodiments of the present technology.

FIG. 2B is a top view of the second portion 201b of the modular physical health testing system 200 illustrated in FIG. 2A. As shown, the system 200 includes a first arrangement of a plurality of physical health testing devices and related objects. In the illustrated embodiment, the plurality of physical health testing devices includes a blood pressure/heart rate cuff and/or monitor 221, a thermometer 222, an electrocardiogram (ECG) device 223, a stethoscope 224, and a glucose and/or cholesterol blood test device 225. The system 200 further can include a communications hub 215 ("the hub 215"), one or more glucose tests strips 225a, one or more lipids test strips 225b, one or more sterile wipes 231, one or more finger lancets 232, one or more capillary collectors 233, and a disposal bag or container 240.

Figure 2C:
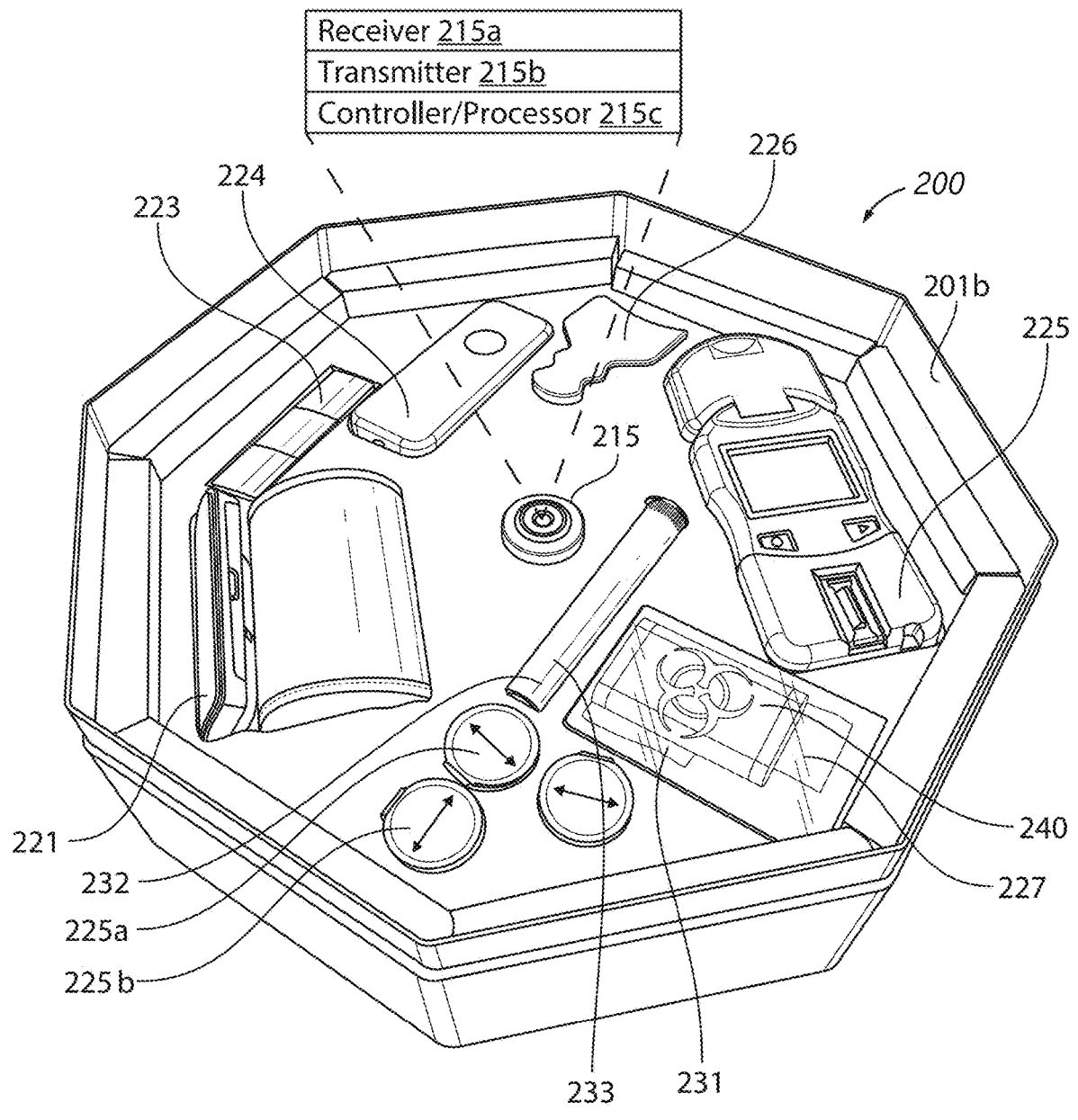
FIG. 2C is a partially schematic top perspective view of the modular physical health testing system of FIG. 2A configured in accordance with some embodiments of the present technology.

In some embodiments, one or more of the health testing devices may be omitted and/or the system 200 can include additional physical health testing devices and/or related objects in addition to or in lieu of the physical health testing devices and related objects illustrated in FIG. 2B. For example, FIG. 2C is a top perspective view of the second portion 201b of the modular physical health testing system 200 illustrated FIG. 2A depicting a second arrangement of a plurality of physical health testing devices and related objects. The system 200 illustrated in FIG. 2C is similar to the system 200 illustrated in FIG. 2B. Therefore, similar reference numbers are used to indicate similar elements across FIGS. 2B and 2C, but the individual devices and components may not be identical. The system 200 illustrated in FIG. 2C, further includes a tape measure 226 and bandages 227 (e.g., Band-aids), and does not illustrate and/or does not include a thermometer 222. The systems 200 illustrated in FIGS. 2B and/or 2C may include a scale, vision testing systems, dermatological screening systems, cameras, other blood tests, and/or other first aid medical supplies (e.g., gauze) in addition to or in lieu of one or more of the illustrated physical health testing devices. In these and other embodiments, the systems 200 illustrated in FIGS. 2B and/or 2C may include a camera or other imaging device (e.g., with or without one or more filters), an otoscope, a phoropter, a microscope (e.g., slit-lamp microscope), a tonometer, applanation instruments, an ultrasound device, an eye chart (e.g., a Snellen Chart), a refractor, an ophthalmoscope, a keratometer, a lensometer, a retinoscope, a vision screener, a pachymetry device, an occluder, a pupillary distance meter, a scleral depresser, and/or one or more other ophthalmic physical health testing devices, supplies (e.g., eye drops), and/or related objects (e.g., stands, chin rests, illumination sources, etc.) in addition to or in lieu of one or more of the illustrated physical health testing devices. In these and still other embodiments, all or a subset of the physical health testing devices of the plurality of physical health testing devices included in the systems 200 of FIGS. 2B and/or 2C are approved for use by an appropriate governmental administrative body (e.g., in the United States— by the U.S. Food and Drug Administration of the United States Department of Health and Human Services).

Referring to FIGS. 2B and 2C together, the second portion 201b of the system 200 can include one or more (e.g., rechargeable) batteries and/or associated charge ports/wires. Additionally, or alternatively, the second portion 201b can include charge ports/wires configured to charge one or more batteries of or otherwise provide power to one or more of the physical health testing devices.

The hub 215 of the system 200 can include a receiver 215*a*, a transmitter 215*b*, and a controller/processor 215*c*, among other circuitry components. Components of the hub 215 can be positioned within the second portion 201*b* of the housing 201 of the system 200. For example, components of the hub can be positioned within a compartment (not shown) of or a standalone housing (not shown) within the second portion 201*b*. The compartment and/or the standalone housing can be configured to protect one or more components of the hub 215 (e.g., from impact and/or water or other liquids). In some embodiments, the compartment and/or standalone housing includes a stem or protrusion that extends toward a front interface of the second portion 201*b*. Portions of the receiver 215*a*, the transmitter 215*b*, and/or other communication components of the hub can be positioned within the stem or protrusion (e.g., to increase communication signal strength and/or quality between (a) the hub 215 and (b) a software application running on a user device, one of more of the physical health testing devices of the system 200, and/or one or more remote servers/databases).

In operation, the hub 215 is configured to manage communication between individual physical health testing devices, a software application running on a user's device 105 (FIG. 1), and/or one or more remote servers/databases 110 (FIG. 1) or other devices 105. In this regard, individual ones of the plurality of physical health testing devices, the device(s) 105, and/or the remote servers/databases 110 can directly or indirectly communicate with the hub 215 over one or more wired or wireless connections. For example, individual ones of the plurality of physical health testing devices, the device(s) 105, and/or the remote servers/databases 110 can be paired with the hub 215 and can communicate with the hub 215 over a Wi-Fi, Bluetooth, Bluetooth Low Energy ("BLE"), Zigbee, hardwire, and/or other communication means. As a more specific example, individual ones of the plurality of physical health testing devices can communicate device initialization/startup information, status data, health data related to a user, and/or other information directly to the hub 215 (e.g., via a Bluetooth connection). In turn, the hub 215 can communicate all or a subset of the information (e.g., health data) to one or more devices 105 (e.g., a user's mobile device 105*e* that is currently running a related software application) paired with the hub 215 and/or directly or indirectly (e.g., via one or more devices 105) to one or more remote servers/databases 110 (e.g., for storage in database entries associated with a user). Additionally, or alternatively, individual ones of the plurality of physical health testing devices can communicate generated health data directly to one or more connected devices 105, which in turn can communicate all or a subset of the received health data to the hub 215 and/or to one or more remote servers/databases 110.

More specifically, the hub 215 is configured to communicate with one or more peripheral devices, circuits, and/or components of the system 200. For example, the hub 215 can be configured to execute instructions stored in memory, including various processes, logic flows, and routines for controlling operation of the system 200 and/or for managing communications between the various electrical circuits and devices on and/or connected to the system 200. In some embodiments, memory used to store the instructions can include electrically erasable programmable read-only memory ("EEPROM"), double data rate (any generation) dynamic random-access memory ("DDR DRAM"), and/or NAND flash memory ("NAND flash"). The EEPROM, for example, can be configured to store boot instructions of the system 200. The DDR DRAM can permit high speed data transfers while the system 200 remains powered on and/or while power is supplied to the system 200. The NAND flash can provide non-volatile memory storage (e.g., to store system, user, and/or other information).

Peripheral devices, circuits, and/or components in communication with the hub 215 can include various communication devices, circuits, and/or components on and/or connected to the system 200. For example, the system 200 can include Wi-Fi and/or Bluetooth controller(s). A Wi-Fi controller (e.g., an IEEE 802.11 b/g/n/RF/Baseband/Medium Access Control (MAC) link controller) can allow the system 200 to wirelessly connect to the internet. In some embodiments, the Wi-Fi controller can wirelessly connect to the internet by leveraging TV white space channels. A Bluetooth controller (e.g., a Bluetooth 4.0 compliant module or controller) can allow the system 200 to communicate with Bluetooth compatible devices. In some embodiments, the Bluetooth module can be optimized for low power consumption. In some embodiments, the system 200 can include an Wi-Fi and/or Bluetooth antenna to improve signal strength.

Figure 3:
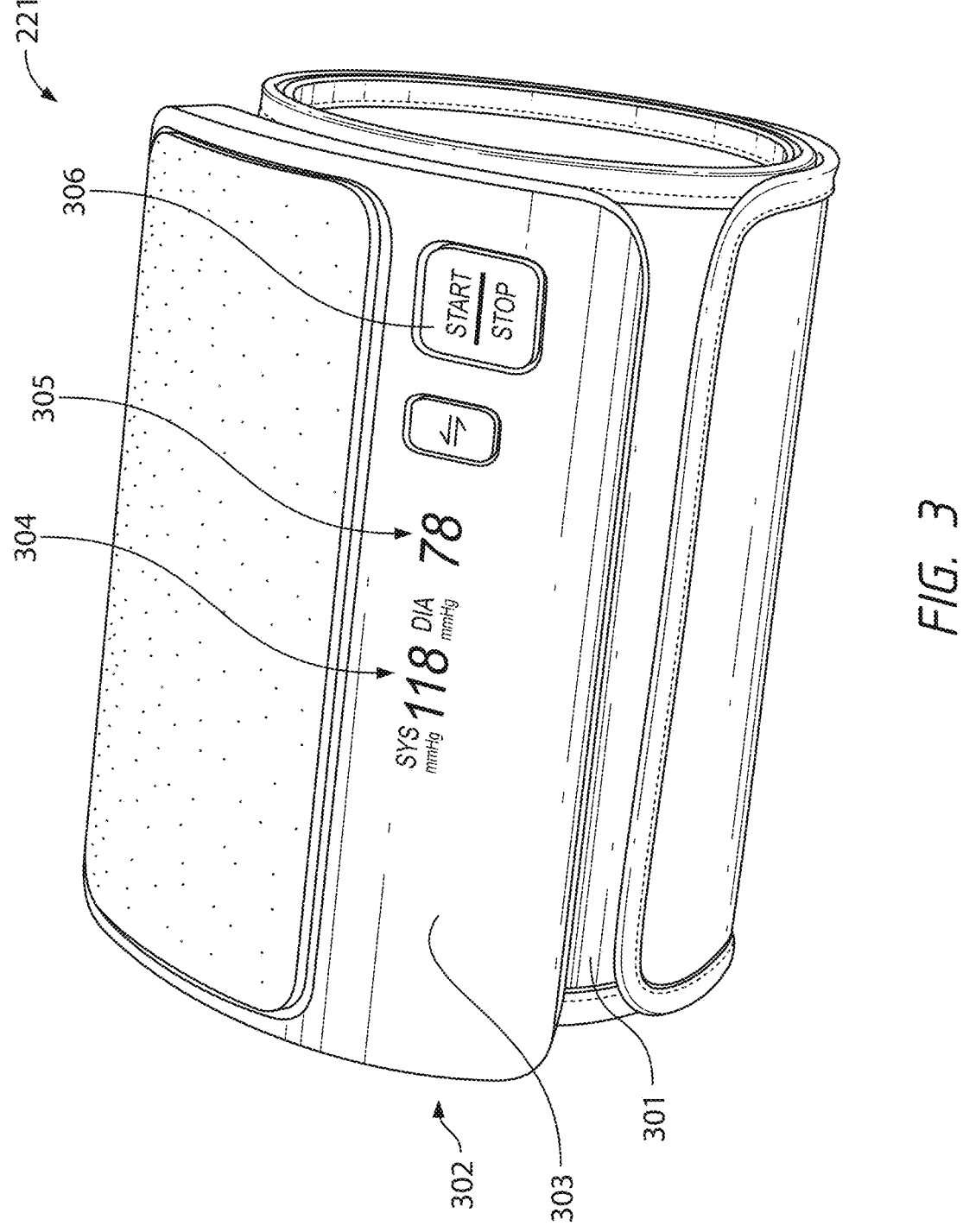
FIG. 3 is a perspective view of a blood pressure and/or heart rate cuff and/or monitor of a modular physical health testing system configured in accordance with various embodiments of the present technology.

FIG. 3 is a perspective view of the heart rate and/or blood pressure cuff and/or monitor 221 ("the BP/HR cuff 221") of the modular physical health testing system 200 (FIGS. 2A,2B, and/or 2C) configured in accordance with various embodiments of the present technology. As shown, the BP/HR cuff 221 includes an arm strap 301 that when rolled defines a cavity 302, a display 303, and a start/stop button 306. The arm strap 301 may be integrated into the housing 201 (FIG. 2A) and/or otherwise attached thereto. The display 303 is configured to provide visual feedback of a user's blood pressure and/or heart rate during use of the BP/HR cuff 221. For example, the display 303 can provide visual feedback 304 of a user's systolic blood pressure and/or visual feedback 305 of the user's diastolic blood pressure. In these and other embodiments, the display 303 can provide other visual feedback, such as an indication (not shown) of a user's heart rate and/or an indication (not shown) that the BP/HR cuff 221 has been successfully paired with the hub 215 (FIGS. 2B and/or 2C) and/or with a user's device 105 (FIG. 1) running a related software application. In some embodiments, the display 303 may be integrated into the housing 201 (FIG. 2A) and/or provided on the user device 105. In some embodiments, the BP/HR cuff 221 can be an EVOLV™ Automatic Blood Pressure Monitor manufactured by Omron® based in Kyoto, Japan. In other embodiments, the BP/HR cuff 221 of the system 200 can be another blood pressure and/or heart rate cuff and/or monitor.

In operation, a user places his/her arm in the cavity 302 defined by the strap 301 of the BP/HR cuff 221. Once positioned on the user's arm and after the user presses the start/stop button 306 (e.g., when the user is sitting down), the strap 301 compresses about the user's arm and conducts several readings to determine the user's heart rate and/or blood pressure. The BP/HR cuff 221 then communicates all or a subset of this health data to the hub 215 (FIGS. 2B and/or 2C) and/or to the user's device 105 running the related software application (e.g., directly and/or via the hub 215).

Figure 4:
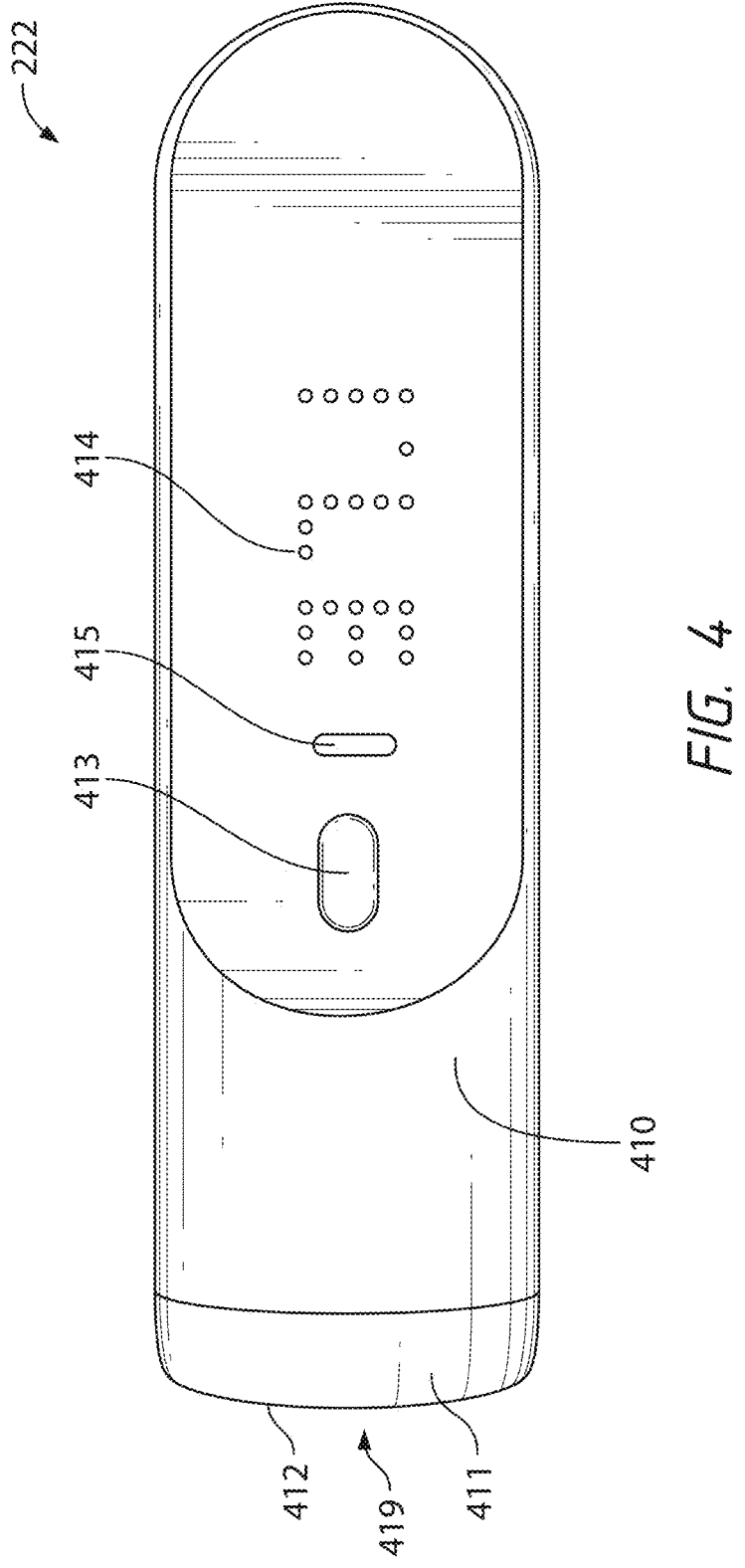
FIG. 4 is a front view of a thermometer of a modular physical health testing system configured in accordance with various embodiments of the present technology.

FIG. 4 is a front view of the thermometer 222 of the modular physical health testing system 200 (FIGS. 2A, 2B, and/or 2C) configured in accordance with various embodiments of the present technology. The thermometer includes a body or housing 410, one or more infrared temperature sensors (not shown), a removable/replaceable/sterilizable sensor cap 411 defining a cavity 419 that exposes the temperature sensor(s), a start/stop button 413, a display 414, and a visual indicator 415. The display 414 is configured to provide visual feedback of a user's internal body temperature (e.g., in degrees Celsius, in degrees Fahrenheit, etc.). In these and other embodiments, the display 414 can provide other visual feedback, such as an indication (not shown) that the thermometer 222 has been successfully paired with the hub 215 (FIG. 2B and/or 2C) and/or with a user's device 105 (FIG. 1) running a related software application. The visual indicator 415 is configured to provide color-coded feedback to a user that a measured internal body temperature either falls within or falls outside of a normal and healthy temperature range. In some embodiments, the display 414 may be integrated into one or more displays viewable on the housing 201 (FIG. 2A) and/or provided on the user device (FIG. 1). In some embodiments, the thermometer 222 can be a Thermo Smart Temporal Thermometer manufactured by Nokia® based in Espoo, Finland. In other embodiments, the thermometer 222 of the system 200 can be another thermometer. Furthermore, although the thermometer 222 illustrated in FIG. 4 is an infrared thermometer, the thermometer 222 in other embodiments can be another type of analog or digital thermometer.

In operation, a user presses the start/stop button 413, places a surface 412 of the sensor cap 411 against his/her forehead near one of his/her temples, and drags the surface 412 across his/her forehead until the thermometer 222 pulsates to indicate that the thermometer 222 has obtained a temperature reading. The thermometer 222 displays a measured temperature on the display 414 and presents a color-coded indication using the visual indicator 415 (e.g., green if the measured temperature falls within a normal temperature range, yellow if the measured temperature falls slightly outside of the normal temperature range, and/or red if the measured temperature falls well outside of the normal temperature range). In these and other embodiments, the thermometer 222 then communicates all or a subset of this health data to the hub 215 (FIGS. 2B and/or 2C) and/or to the user's device 105 running the related software application (e.g., directly and/or via the hub 215).

Figure 5:
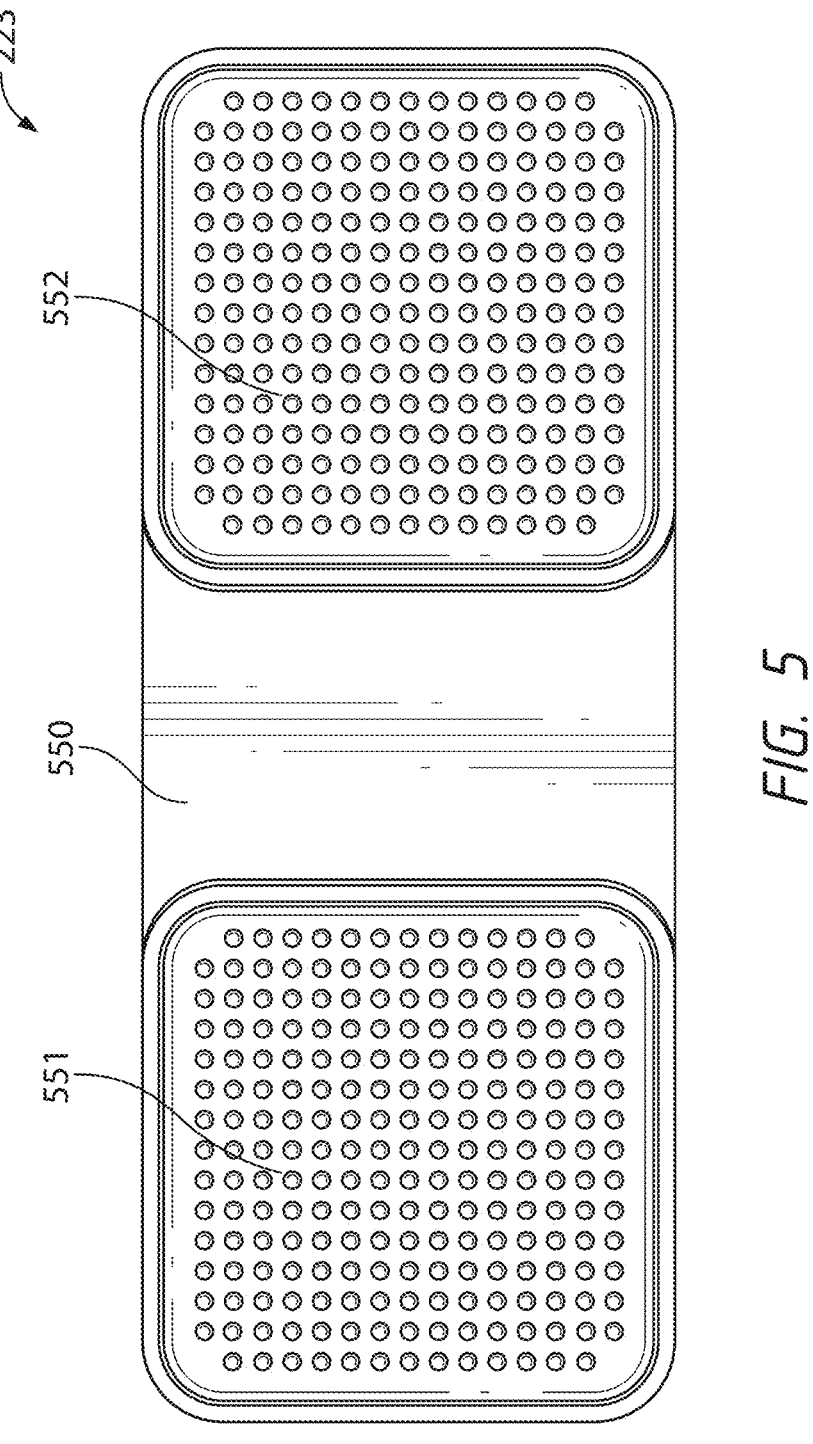
FIG. 5 is a front view of an electrocardiogram device (ECG or EKG device) of a modular physical health testing system configured in accordance with various embodiments of the present technology.

FIG. 5 is a front view of the ECG or EKG device 223 of the modular physical health testing system 200 (FIGS. 2A, 2B, and/or 2C) configured in accordance with various embodiments of the present technology. As shown, the ECG device 223 is a mobile ECG device that includes a body or housing 550, a first electrode 551, and a second electrode 552. In some embodiments, the ECG device 223 can be a Kardia™ Mobile EKG or ECG device manufactured by AliveCor® based in Mountain View, California. In other embodiments, the ECG device 223 of the system 200 can be another ECG device.

In operation, a user (i) places the ECG device 223 on his/her chest or (ii) places one finger on the first electrode 551 and another finger on the second electrode 552. Using the first and second electrodes 551 and 552, the ECG device 223 records and stores a single-channel ECG rhythm. In some embodiments, the ECG device 223 then communicates all or a subset of this health data to the hub 215 (FIGS. 2B and/or 2C) and/or to the user's device 105 (FIG. 1) running the related software application (e.g., directly and/or via the hub 215) for further processing and analysis. In some embodiments, the ECG device 223 can be operably coupled to one or more displays viewable on the housing 201 (FIG. 2A) and/or on the user device 105.

Figures 6A, 6B, 6C:
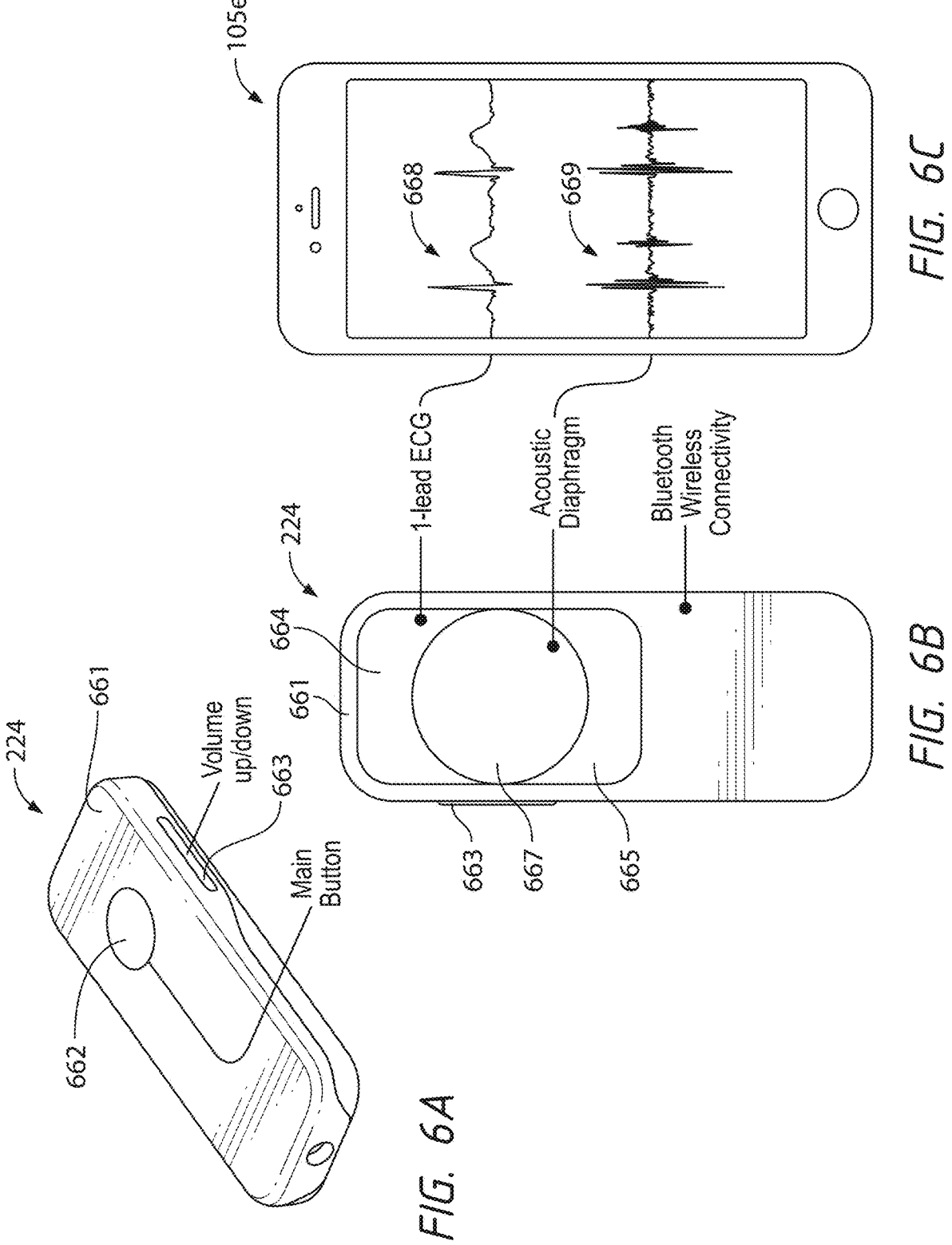
FIGS. 6A and 6B are a perspective view and a back view, respectively, of a stethoscope of a modular physical health testing system configured in accordance with various embodiments of the present technology.
FIG. 6C is a front view of a mobile ECG device running a software application related to a modular physical health testing system in accordance with various embodiments of the present technology.

FIGS. 6A and 6B are a perspective view and a back view, respectively, of the stethoscope 224 of the modular physical health testing system 200 (FIGS. 2A, 2B, and/or 2C) configured in accordance with various embodiments of the present technology. As shown, the stethoscope 224 includes a housing or body 661, a main button 662, volume control buttons 663, a first electrode 664, a second electrode 665, and an acoustic diaphragm 667. The illustrated stethoscope 224 is a digital stethoscope. In some embodiments, the stethoscope 224 can be a DUO™ Model E5 System or a CORE™ Model E4 System manufactured by Eko® based in New York, New York. In other embodiments, the stethoscope 224 can be a Littmann® Electronic Stethoscope Model 3200 manufactured by 3M® based in Maplewood, Minnesota. In still other embodiments, the stethoscope 224 of the system 200 can be another digital or analog stethoscope.

In operation, a user places the first electrode 664 and the second electrode 665 against his/her chest and presses the main button 662 to start collection of health data related to the user's heart. The first and second electrodes 664 and 665 measures the electrical activity of the user's heart to generate an ECG while the acoustic diaphragm 667 records sounds and murmurs made by the user's heart to generate a phonocardiogram (PCG). In some embodiments, the ECG device 223 then communicates all or a subset of this health data to the hub 215 (FIGS. 2B and/or 2C) and/or to the user's device 105 running a related software application (e.g., directly and/or via the hub 215) for further processing and analysis. For example, FIG. 6C is a front view of a user's mobile device 105e illustrating a 1-lead ECG recording 668 and a PCG recording 669 in accordance with various embodiments of the present technology and received from the hub 215 and/or from the stethoscope 224. In some embodiments, the stethoscope 224 and/or the ECG device 223 can be operably coupled to one or more displays viewable on the housing 201 (FIG. 2A) and/or on the user device 105.

Figure 7:
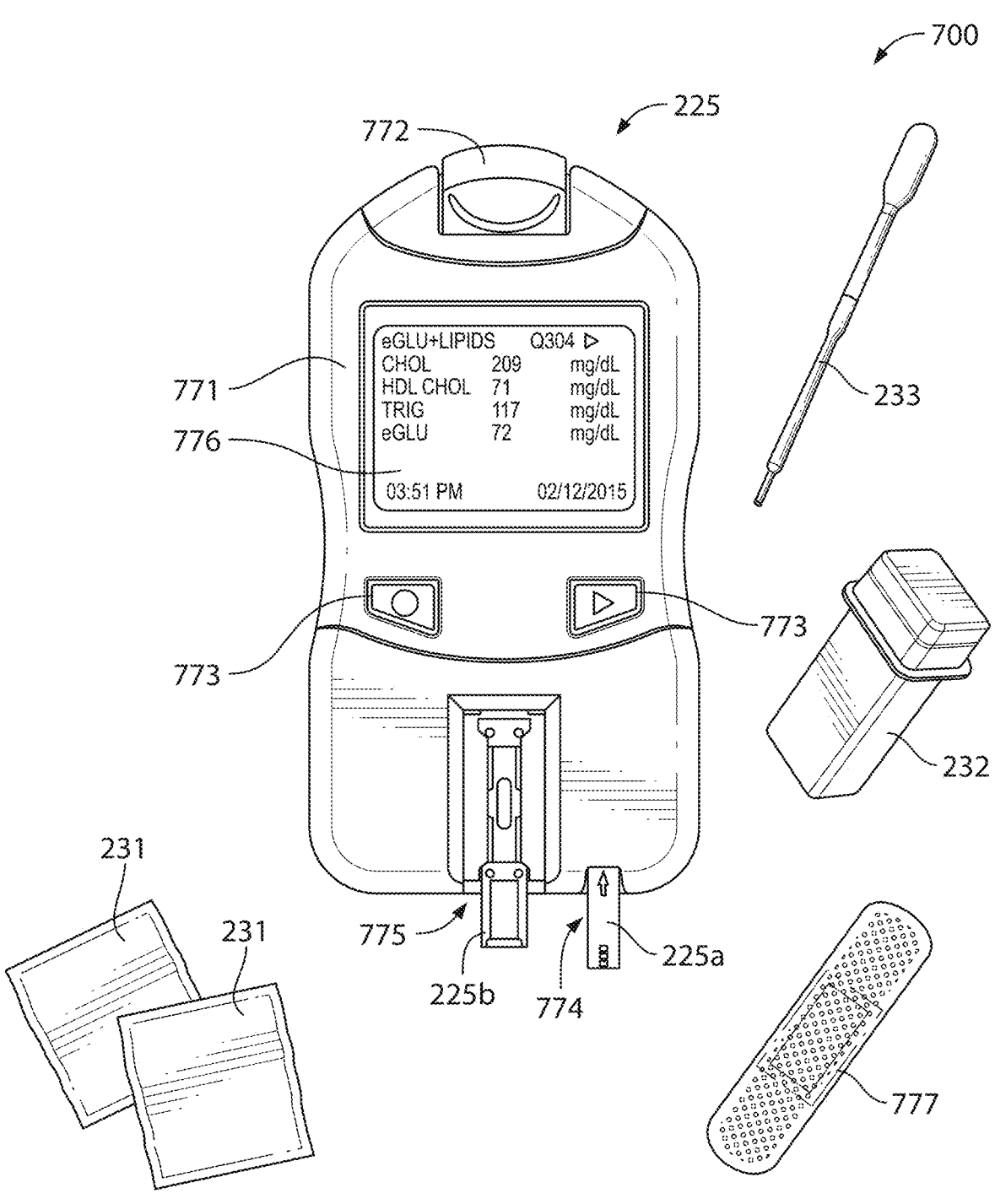
FIG. 7 is a perspective view of a blood test system of a modular physical health testing system configured in accordance with various embodiments of the present technology.

FIG. 7 is a perspective view of a blood test system 700 of the modular physical health testing system 200 (FIGS. 2A, 2B, and/or 2C) configured in accordance with various embodiments of the present technology. As shown, the blood test system 700 includes the glucose and/or cholesterol blood test device 225, the glucose test strip(s) 225a, the lipids test strip(s) 225b, the alcohol wipe(s) 231, the finger lancet 232, the capillary collector(s) 233, and a Band-aid 777. The glucose and/or cholesterol blood test device 225 includes a housing or body 771, a communications dongle 772, input and menu navigation buttons 773, a glucose test strip recess 774, a lipids test strip recess 775, and a display 776. The display 776 is configured to provide visual feedback of health data related to a user's blood during use of the glucose and/or cholesterol blood test device 225. For example, the display 776 can provide visual feedback of a user's high-density lipoprotein (HDL) cholesterol levels, low-density lipoprotein (LDL) cholesterol levels, total cholesterol levels, ratios of HDL to LDL, triglyceride (TRIG) levels, lipids levels, and/or glucose (eGLU) levels. In these and other embodiments, the display 303 can provide other visual feedback, such as an indication (not shown) of a user's heart rate and/or an indication (not shown) that the glucose and/or cholesterol blood test device 225 has been successfully paired with the hub 215 (FIG. 2B) and/or with a user's device 105 (FIG. 1) running a related software application. The communications dongle 772 is configured to removably engage with the housing 771 and to permit the glucose and/or cholesterol blood test device 225 to communicate with the hub 215 (FIGS. 2B and/or 2C) and/or with a device 105 (FIG. 1) running a related software application (e.g., directly and/or via the hub 215). In some embodiments, the glucose and/or cholesterol blood test device 225 is a CardioChek Plus™ Cholesterol and Glucose Monitor manufactured by PTS Diagnostics® based in Whitestown, Indiana. In other embodiments, the glucose and/or cholesterol blood test device 225 of the system 200 is another glucose and/or cholesterol blood test device. In some embodiments, the blood test system 700 can be used to determine other characteristics discernable via a blood test, such as red blood cell count, white blood cell count, platelets, hemoglobin, hematocrit, calcium, electrolytes, blood enzymes, and/or other characteristics that provide insights on patient health information (e.g., genetic testing, chromosome analysis, etc.).

In operation, a user powers the glucose and/or cholesterol blood test device 225 on and loads a glucose test strip 225a and a lipids test strip 225b into the glucose test strip recess 774 and the lipids test strip recess 775, respectively. To test the user's glucose levels, the user cleans one of his/her fingers using an alcohol wipe 231, pricks or punctures his/her finger using the finger lancet 232, squeezes a drop of blood out of their finger, and places the drop of blood onto the glucose test strip 225a. To test the user's lipids levels, the user either (i) cleans one of his/her fingers using an alcohol wipe 231 and pricks or punctures his/her finger using the finger lancet 232 or (ii) squeezes more blood out of the finger he/she pricked or punctured when performing the glucose test. The lipids test, however, typically requires more blood than the glucose test. As such, the user uses the capillary collector 233 to collect a relatively larger amount of blood than the single drop required for the glucose test. Using the capillary collector 233, the user then squirts the collected blood onto the lipids test strip 225b. The user may then apply the Band-aid 777 over the pricked or punctured finger to stop any bleeding. The glucose and/or cholesterol blood test device 225 analyzes the blood submitted onto the test strips 225a and 225b, generates health data related to the user's blood, displays all or a subset of the health data on the display 776, and/or communicates all or a subset of the health data to the hub 215 and/or to a user's device 105 running a related software application (e.g., directly and/or via the hub 215).

The user may further dispose of any waste from the glucose and/or cholesterol blood test in the disposal bag or container 240 of the system. For example, the user may dispose of the glucose test strip 225a, the lipids test strip 225b, the alcohol wipe(s) 231, the finger lancet 232, the capillary collector(s) 233, and/or a packaging (not shown) of the Band-aid 777 in the disposal container 240. In some embodiments, the disposal container 240 is a hazardous waste disposal container 240 configured in accordance with governmental regulations. For example, the disposal container 240 can include a one-way slot or lid such that waste submitted into the disposal container 240 cannot be retrieved out of the disposal container 240 without a key or destruction of the disposal container 240. In these and other embodiments, the disposal bag or container 240 can be made of a suitable material that is water- and/or chemical-resistant, and/or that is sterilizable, such as plastic.

Figure 8:
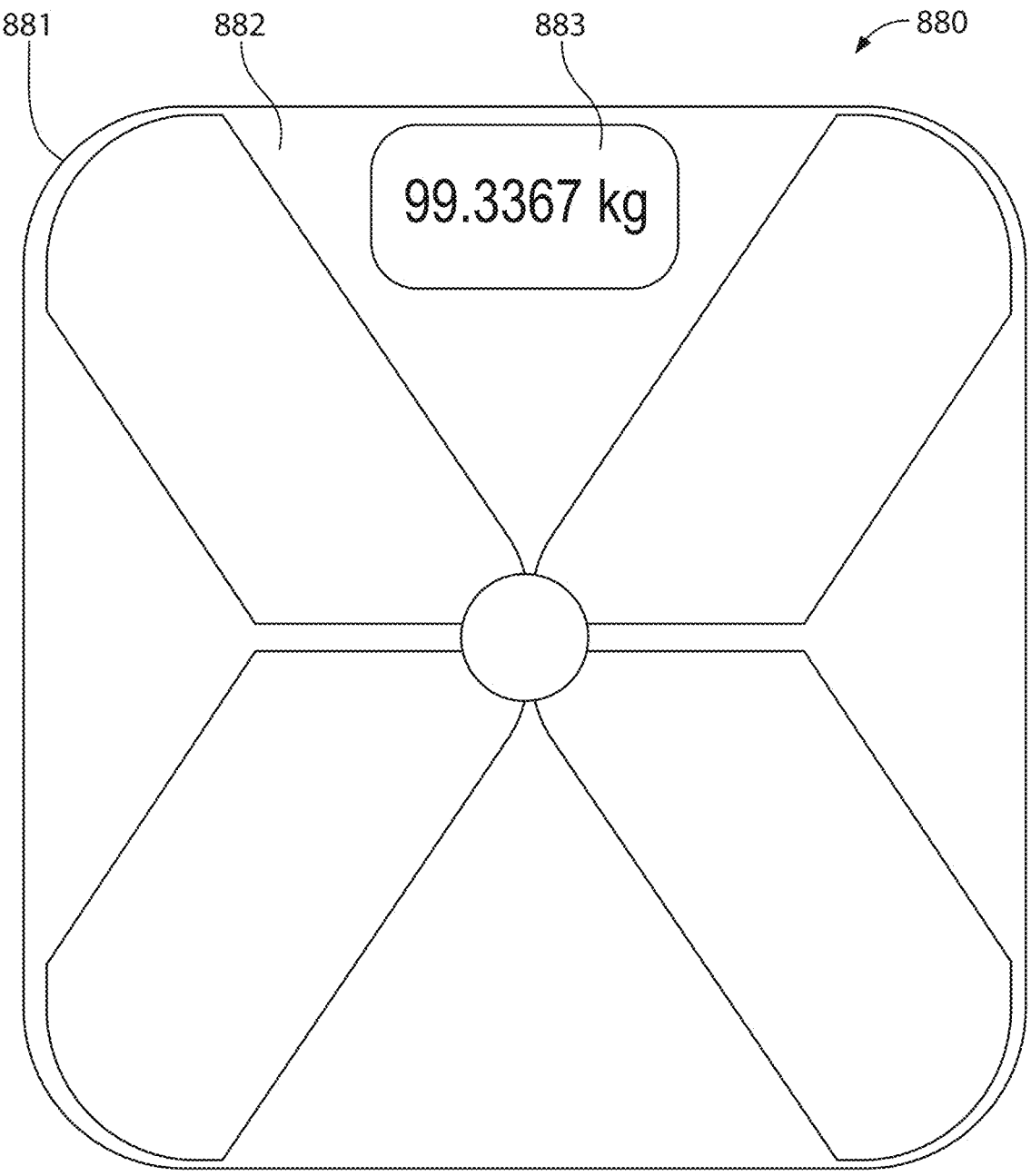
FIG. 8 is a front view of a scale of a modular physical health testing system configured in accordance with various embodiments of the present technology.

FIG. 8 is a front view of a scale 880 of a modular physical health testing system 200 configured in accordance with various embodiments of the present technology. As shown, the scale includes a housing or body 881, a top surface 882, and a display 883. The display 883 is configured to provide visual feedback of health data related to a user's weight during use of the scale 880. For example, the display 883 can provide visual feedback of a user's weight in kilograms or pounds. In these and other embodiments, the display 883 can provide other visual feedback, such as an estimation (not shown) of a user's body mass index (BMI) and/or an indication (not shown) that the scale 880 has been successfully paired with the hub 215 (FIGS. 2B and/or 2C) and/or with a user's device 105 (FIG. 1) running a related software application (e.g., directly and/or via the hub 215). The scale 880 illustrated in FIG. 8 is a digital scale. In some embodiments, the scale 880 can be a ESF17 Smart Fitness Scale manufactured by Etekcity® based in Anaheim, California. In other embodiments, the scale 880 of the physical health testing system 200 can be a Comper™ Smart Weight Scale manufactured by Comper Chuangxiang Technology Co., Ltd based in Beijing, China, or another digital scale. In still other embodiments, the scale 880 can be an analog or other type of scale.

FIG. 9 is a flow diagram illustrating a physical exam routine 900 using a modular physical health testing system configured in accordance with various embodiments of the present technology. In some embodiments and as described below, the routine 900 can be executed, at least in part, by various components of the system 200 described above with reference to FIGS. 1-8. In these and other embodiments, the routine 900 can be executed, at least in part, by one or more devices 105 (FIG. 1), such as by a user's mobile device 105e running a related software application. In these and still other embodiments, the routine 900 can be executed, at least in part, by one or more remote servers/databases 110 (FIG. 1), by a user of the system 200, and/or by a supplier or vendor of the system 200.

For the sake of example only, the routine 900 is discussed in detail below in the context of one or more users who subscribe to a service offered by a supplier or vendor. In particular, the service is an agreement to supply (e.g., send in the mail) a modular physical health testing system 200 to a user (e.g., once, twice, or more per year). After creating an account associated with the service, the user performs a physical exam each time he/she is supplied the system 200 to generate data corresponding to his/her physical health. Once the user has completed the physical exam, the user returns the system 200 (e.g., in the mail) to the supplier or vendor. In this manner, users are able to run a variety of physical health tests from any location (e.g., at home, at work, at a hotel, at an assisted living facility, at a gym, at school) and/or at a time that is convenient for him/her, thereby obviating the practice and inconvenience of scheduling and attending a doctor's appointment for a physical exam. Furthermore, because the physical exam can be performed outside of a hospital or medical facility and/or without supervision of a healthcare professional, users can undergo a physical exam without unexpected hospital bills. In addition, the modular physical health testing systems free up healthcare time, funds, and resources to be spent on treating patients with more acute needs. In turn, users are more likely to stay current on their routine physical exams, increasing the chances of early detection of medical concerns and generating a wealth of medical history data for healthcare professionals to consult when a patient does become ill. To incentivize participation in the service, insurance companies can offer a discount on participating users' or companies' health insurance premiums (e.g., equal to or greater than the cost of subscribing to the service).

At block 901, the routine 900 begins when a user creates an account and subscribes to a service in which a modular health testing system is provided to the user at a specified frequency. In some embodiments, the user visits a website and/or downloads a software application (e.g., a mobile application) to create the account and/or to subscribe to the service. In these and other embodiments, the user creates an account by registering his/her contact information (e.g., email address) and setting a security feature (e.g., password) that allows for subsequent access to the account. The account can be unique to the user such that any health data generated by a modular health testing system can be associated with the user via the account and stored for future reference, analysis, and/or review. In some embodiments, a single account (e.g., a family account) can be associated with more than one user (e.g., with a husband and a wife), for example, by setting up separate usernames for each of the users. In these embodiments, health data generated by a modular health testing system can be associated with only one username associated with the account at a time and stored for future reference, analysis, and/or review. Once an account is created, the user can subscribe to the service by (a) specifying a subscription tier to, for example, (i) select a specific combination of physical health testing devices to be included in each modular health testing system and/or (ii) select a specific combination of available features, such as an individual or a family plan; (b) specifying a frequency (e.g., once, twice, or more per year) at which a modular health testing system is to be provided to the user; (c) specifying a mailing address; and/or (d) specifying a method of payment.

At block 902, the routine 900 continues by stocking and/or charging a plurality of physical health testing devices, a communications hub, and/or related objects in a modular physical health testing system to be provided to the user. In some embodiments, the routine 900 can stock specific physical health testing devices into the modular system in accordance with the user's account and/or subscription tier. For example, the routine 900 can (i) stock a BP/HR cuff and/or monitor, a thermometer, an ECG or EKG device, a stethoscope, a tape measure, and/or a glucose and/or cholesterol blood test device into the modular system in accordance with a first tier subscription plan; and/or (ii) stock these physical health testing devices along with a scale and/or other physical health testing devices into a modular system in accordance with a second tier (e.g., more expensive) subscription plan. In these and other embodiments, the routine 900 can stock physical health testing devices into the modular system by removing from the system physical health testing devices previously sent to and/or used by another user, cleaning and sterilizing the physical health testing devices, and replacing the physical health testing devices back into the system (e.g., into the second portion of the housing of the system). In these and still other embodiments, the routine 900 can stock the system by removing waste included in the disposal container of the modular system; cleaning/sterilizing the disposal container, a finger lancet, and/or capillary collector(s); and/or stocking the modular system with related objects (e.g., with alcohol wipe(s), capillary collector(s), finger lancet(s), and/or bandages).

The routine 900 can charge the physical health testing devices and/or the communications hub by replacing batteries in the physical health testing devices and/or the hub, and/or by charging rechargeable batteries included within the physical health testing devices and/or the hub. In these and other embodiments, the routine 900 can charge the physical health testing devices by replacing batteries and/or by charging one or more rechargeable batteries included in the modular system. In turn, the batteries of the system can charge the batteries of individual physical health testing devices included in the system. Alternatively, the hub and/or one or more of the physical health testing devices can be powered by connecting the modular system, the hub, and/or the one or more devices to a power supply (e.g., by plugging a corresponding power cord into a power outlet).

At block 903, the routine 900 continues by syncing or registering the communications hub of the modular system with the physical health testing devices and/or with the user's account. In some embodiments, the routine 900 syncs the physical health testing devices with the hub by connecting the physical health testing devices to the hub over a network (e.g., using one or more wired connections and/or Wi-Fi, Bluetooth, or another wireless communication protocol) such that the physical health testing devices are placed in wired and/or wireless in communication with the hub and are thereby registered to the hub. In these and other embodiments, the routine 900 registers the modular physical health testing system (e.g., the hub of the modular system) to a specific user's account (e.g., such that the modular system is operable only by the user and only when the user (i) logs into his/her account on a related software application (block 905) and (ii) connects the software application to the communications hub of the modular system (block 906)).

At block 904, the routine 900 continues by supplying the modular physical health testing system to the user. In some embodiments, the routine 900 can supply the modular system to the user by shipping the modular system to the user (e.g., at the user's home or at another location). In these and other embodiments, the routine 900 can supply the modular system to the user via other means (e.g., by making the system available for checkout to the user, such as at a pharmacy or hospital).

At block 905, the routine 900 continues when the user downloads a software application related to the modular physical health testing system onto a user device. For example, a user can download a mobile application or another software application to a user's mobile device. In some embodiments, the modular system includes directions or a QR code to aid the user in downloading the software application.

Once downloaded, the software application can require the user to log into their account. FIG. 10A is a partially schematic view of a login user interface (UI) of the software application in accordance with various embodiments of the present technology. As shown, the user can log into his/her account using the email address and password credentials associated with (e.g., used to create) the account.

In some embodiments, after the user logs into his/her account, the user can be presented with one or more terms of service, privacy, and/or marketing opt in acceptance UIs of the software application. FIG. 10B illustrates a partially schematic view of such a UI in accordance with various embodiments of the present technology. As shown, the user can be asked to confirm (a) that he/she is at least 18 years of age, (b) that he/she consents to the terms of service and to the collection, processing, and/or disclosure of his/her health data, and/or (c) that he/she consents to receiving marketing communications from a company associated with the modular system. Indications (e.g., a date and/or timestamp) of one or more of the user's confirmations can be stored for later reference.

In these and other embodiments, after the user logs into his/her account, the user can be presented with one or more user info verification UIs of the software application. FIG. 10C illustrates a partially schematic view of such a UI in accordance with various embodiments of the present technology. As shown, the user can be requested to verify the user's name, date of birth, gender, mailing address, and/or phone number. One or more pieces of user information entered and/or verified by the user can be stored for later reference.

In these and still other embodiments, after the user logs into his/her account, the user can be presented with one or more health care information UIs of the software application. FIG. 10D illustrates a partially schematic view of such a UI in accordance with various embodiments of the present technology. As shown, the user can be requested to (a) enter and/or verify whether he/she has a primary care physician; (b) enter and/or verify whether he/she has health insurance; and/or (c) indicate why the user decided to try the modular system service. In some embodiments, if the user indicates that he/she has a primary care physician, the user can be requested to provide and/or verify the physician's contact information (e.g., so that health data generated by the modular system can be forwarded to the physician for review and/or to update the user's medical history). In these and other embodiments, if the user indicates that he/she has health insurance, the user can be requested to (i) enter and/or verify the type of health insurance and/or (ii) provide and/or verify his/her health insurance information. One or more pieces of healthcare information entered and/or verified by the user can be stored for later reference.

In these and yet other embodiments, after the user logs into his/her account, the user can be presented with one or more lifestyle questionnaire UIs of the software application. FIG. 10E illustrates a partially schematic view of such a UI in accordance with various embodiments of the present technology. As shown, the user can be requested to enter and/or verify his/her (a) ethnicity; (b) activity level (e.g., frequency of physical exercise); (c) forms of physical exercise; (d) diet; (e) average hours of sleep; (f) alcohol consumption frequency; (g) tobacco use frequency; and/or (h) stress level. One or more pieces of lifestyle information entered and/or verified by the user can be stored for later reference.

At block 906, the routine 900 continues by connecting the software application to the hub of the modular system. In some embodiments, the routine 900 connects the software application to the hub over a network (e.g., using one or more wired connections and/or Wi-Fi, Bluetooth, or another wireless communication protocol) such that the software application on the user's device is placed in communication with the hub. As a specific example, the software application running on the user's device can instruct the device to scan for and connect to the modular system via Bluetooth. In response, the modular system can provide the device a notification that connection was successful. In some embodiments, the user device can request (and the modular system can provide) connection characteristic information (e.g., Bluetooth Low Energy characteristic information). After the user device connects to the modular system, the software application can subscribe to status and test result notifications of specific physical health testing devices included in the modular system (e.g., all of the physical health testing devices included in the modular system or only those physical health testing devices that correspond to the user's account or subscription tier). Example notifications include battery status info of the hub and/or of one or more of the physical health testing devices, firmware information of the physical health testing devices and/or of sensors included in the physical health testing devices, and/or data (e.g., health results and/or errors) generated during one or more physical health tests of the physical exam.

Because the physical health testing devices of the modular system are registered with and are in communication with the hub (block 902), the routine 900 also places the software application on the user's device in communication with the physical health testing devices (via notifications sent to the software application from the hub) when the software application is connected to the hub. The software application can remain connected with the communications hub for the duration of the physical exam. In other embodiments, the software application can intermittently connect to the hub (e.g., when the user initiates one of the physical health tests of the physical exam, after a user indicates that one or more physical health tests of the physical exam are complete, at the end of the physical exam, etc.). In these and other embodiments, the routine 900 can connect the software application directly to individual physical health testing devices of the modular system, and/or the routine 900 can connect the software application to one or more remote servers/databases (e.g., directly or via the hub). By connecting the physical health testing devices to the hub of the modular system, the routine 900 obviates the practice of the user downloading a software application on his/her device (e.g., device 105 illustrated in FIG. 1) dedicated to one or more of the physical health testing devices included in the modular system.

As discussed in greater detail below with respect to blocks 907-913 of the routine 900, the software application can provide the user step-by-step instructions for performing a physical exam using the physical health testing devices and related objects included in the modular system. In particular, the software application can permit a user to control individual physical health testing devices of the modular system, view reports of health data related to the user and generated using the physical health testing devices, store all or a subset of generated health data (e.g., to one or more remote servers/databases and/or associated with the user's account), view healthcare recommendations, and/or share generated health data with a healthcare professional. More specifically, the modular system, in operation, is configured to provide a variety of services to a user and/or to facilitate use of one or more functions, some of which are discussed in greater detail below.

In some embodiments, the user can view, access, and/or interface with several of these services and/or functions via one or more UIs of the software application that can be presented on a screen of the user's device when the software application is open and/or connected to the hub. The UI can include one or more buttons or menu options that correspond to one or more of the physical health tests, services, and/or functions of the system. For example, FIG. 10F illustrates a partially schematic view of a physical exam overview UI of the software application in accordance with various embodiments of the present technology. The physical exam overview UI can provide the user an overview of a sequence of physical health tests that are included in the physical exam. In some embodiments, the physical exam overview UI can be presented to the user before starting each of the physical health tests. In these and other embodiments, the physical exam overview UI can include visual indicators that inform the user (a) which physical health tests have been completed; (b) which physical health tests have yet to be started or completed; and/or (c) which physical health test is next in the sequence of physical health tests of the physical exam.

Figures 10G, 10H, 10I:
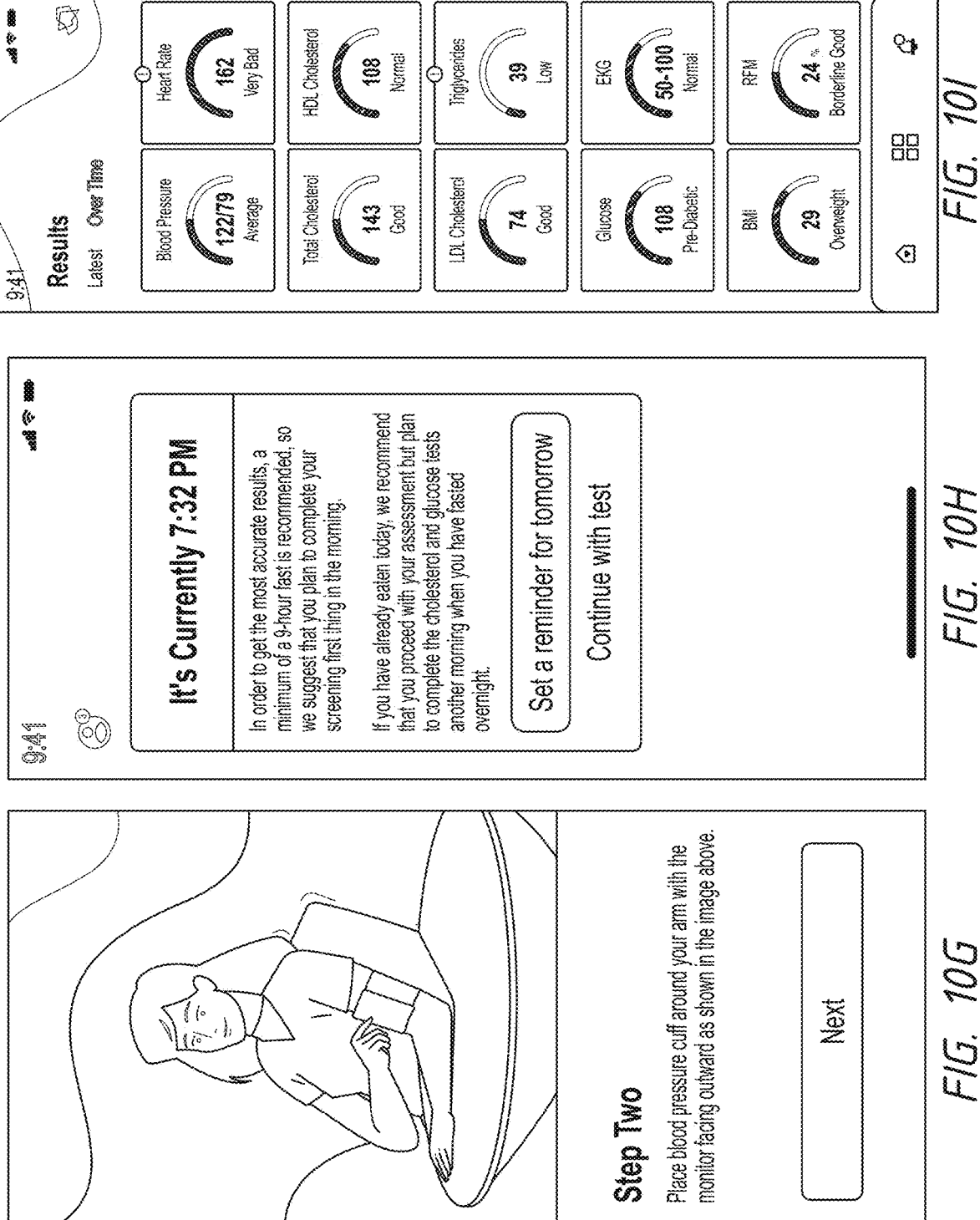
FIGS. 10A-10N are partially schematic views of user interfaces (UIs) of a software application related to a modular physical health testing system in accordance with various embodiments of the present technology.

As a user initiates one of the physical health tests, one or more UIs of the software application can be presented to the user that include step-by-step instructions for performing the corresponding physical health test. FIG. 10G illustrates a partially schematic view of such a UI in accordance with various embodiments of the present technology, that instructs the user to place a blood pressure cuff about his/her arm as part of a blood pressure and/or heart rate physical health test of a physical exam. In these and other embodiments, one or more other UIs of the software application can be presented to the user that include options to start, stop, or skip tests; indicators for whether health data is being generated, for how long to continue generating/collecting health data for a given physical health test, and/or for when health data has been successfully received by the hub or by the software application on the user's device; and/or options to view, share, and/or save generated health data reports.

For the sake of clarity and understanding, specific physical health tests of a physical exam will now be discussed with respect to blocks 907-912 of the routine 900. A person of ordinary skill in the art will readily recognize that the routine 900 can include one or more other physical health tests in addition to or in lieu of one or more of the physical health tests discussed below. For example, the routine 900 in some embodiments can include one or more ophthalmic tests (e.g., eye muscle movement tests to, for example, examine the alignment and movement of a user's eyes; cover tests to, for example, examine movement and coordination of a user's eyes; pupil reaction tests to, for example, examine how a user's pupil adjusts to light and to objects at varying depths; ophthalmic tests to, for example, examine the whites of a user's eye and/or the position of his/her corresponding eyelid; visual acuity tests using, for example, an eye chart; glaucoma tests to, for example, examine fluid pressure within a user's eye; applanation tonometry tests; pachymetry tests to, for example, examine the thickness of a user's cornea; corneal topography tests; visual field (perimetry) tests; fluorescein angiogram tests; diluted pupillary tests; refraction tests to, for example, determine a lens prescription for the user; slit-lamp tests to, for example, examine a user's cornea, iris, lens, sclera, surface, and back of the user's eye and/or the user's corresponding eyelid and eyelashes; and/or one or more other tests, such as diabetic retinopathy tests, macular degeneration tests, cataract tests, ocular hypertension tests, ocular hypotony tests, astigmatism tests, uveitis tests, strabismus tests, retinal tests, etc.) to generate ophthalmic data regarding one or more of the user's eyes in addition to or in lieu of one or more of the physical health tests discussed below.

At block 907, the routine 900 continues when a user initiates a blood pressure and/or heart rate (BP/HR) physical health test of the physical exam to generate the user's blood pressure and/or heart rate data. For example, the user can initiate the BP/HR physical health test by pressing a start button associated with the physical health test that is presented to the user on a UI of the software application. In response, the software application can instruct the hub to connect to a BP/HR cuff and/or monitor of the modular system. In turn, the hub can attempt to connect with the BP/HR cuff and/or monitor. In some embodiments, the hub can instruct the BP/HR cuff and/or monitor to power on before attempting to connect to the BP/HR cuff and/or monitor.

In these and other embodiments, the software application running on the user's device can provide instructions (e.g., via one or more UIs, such as the UI illustrated in FIG. 10G) for performing the BP/HR physical health test, such as instructions for removing the BP/HR cuff and/or monitor from the modular system, turning the BP/HR cuff and/or monitor on, and/or generating BP/HR data corresponding to the user's blood pressure and/or heart rate (e.g., in accordance with the procedure described above with respect to FIG. 3). In this regard, the BP/HR cuff and/or monitor can measure the user's blood pressure and/or heart rate.

After the BP/HR cuff and/or monitor has generated the user's BP/HR data, the BP/HR cuff and/or monitor can enable Bluetooth (or another communication means) and can connect with the hub. When the hub successfully connects with the BP/HR cuff and/or monitor, the hub can notify the user device that connection was successful. In some embodiments, the hub can request (and the BP/HR cuff and/or monitor can provide) connection characteristic information (e.g., Bluetooth Low Energy characteristic information). After the hub receives the characteristic information from the BP/HR cuff and/or monitor, the hub can subscribe to notifications from the BP/HR cuff and/or monitor (e.g., relating to all or specific BP/HR user data). In turn, the BP/HR cuff and/or monitor communicates all requested user BP/HR data to the hub, and the hub then disconnects from the BP/HR cuff and/or monitor. The hub can then communicate the user BP/HR data to the software application running on the user's device. In some embodiments, the hub can format the user BP/HR data it received from the BP/HR cuff and/or monitor before sending the formatted user BP/HR data to the software application. In these and other embodiments, the user can review all or a subset of the user's BP/HR data on the software application (as discussed in greater detail below with respect to block 913). In these and still other embodiments, the routine 900 can store all or a subset of the BP/HR health data (e.g., on one or more remote servers and/or databases, and/or associated with the user's account) using the software application and/or the hub.

At block 908, the routine 900 continues when a user initiates an ECG or EKG physical health test to generate the user's ECG or EKG data. For example, the user can initiate the ECG physical health test by pressing a start button associated with the physical health test that is presented to the user on a UI of the software application. In response, the software application can instruct the hub to connect to an ECG or EKG device of the modular system. In turn, the hub can attempt to connect with the ECG device. In some embodiments, the hub can instruct the ECG device to power on before attempting to connect to the ECG device.

In these and other embodiments, the software application running on the user's device can provide instructions (e.g., via one or more UIs) for performing the ECG physical health test, such as instructions for removing the ECG device from the modular system, turning the ECG device on, and/or generating ECG data corresponding to the user's heart (e.g., in accordance with the procedure described above with respect to FIG. 5). In this regard, the ECG device generates the user's ECG data.

After the ECG device has generated the user's ECG data, the ECG device can enable Bluetooth (or another communication means) and can connect with the hub. When the hub successfully connects with the ECG device, the hub can notify the user device that connection was successful. After the hub connects with the ECG device, the hub can attach to a data stream of one or more sensors of the ECG device. In turn, the ECG device communicates the data stream(s) to the hub. Once the hub has received (e.g., a predetermined amount of) the user's ECG data, the hub can disconnect from the ECG device. The hub can then communicate the user's ECG data to the software application running on the user's device. In some embodiments, the hub can format the user's ECG data it received from the ECG device before sending the formatted user ECG data to the software application. In these and other embodiments, the user can review all or a subset of the user's ECG data on the software application (as discussed in greater detail below with respect to block 913). In these and other embodiments, the routine 900 can store all or a subset of the user's ECG data (e.g., on one or more remote servers and/or databases, and/or associated with the user's account) using the software application and/or the hub.

At block 909, the routine 900 continues when a user initiates a height and/or weight physical health test to generate the user's height and/or weight data. For example, the user can initiate the height and/or weight physical health test by pressing a start button associated with the physical health test that is presented to the user on a UI of the software application. In response, the software application can instruct the hub to connect to a scale and/or another physical health testing device of the modular system associated with the height and/or weight physical health test. In turn, the hub can attempt to connect with the scale and/or with the other physical health testing device. In some embodiments, the hub can instruct the scale and/or the other physical health testing device to power on before attempting to connect to the scale and/or the other physical health testing device. Alternatively, the software application can request that the user perform the height and/or weight physical health test without instructing the hub to connect to a scale or another physical health testing device associated with the height and/or weight physical health test. In these and other embodiments, the software application can request the user to manually enter one or more components of his/her height and/or weight data after performing the height and/or weight physical health test.

In some embodiments, the software application running on the user's device can provide instructions (e.g., via one or more UIs) for performing the height and/or weight physical health test, such as instructions for removing a tape measure, a scale, and/or another physical health testing device associated with the height and/or weight physical health test from the modular system; turning the scale and/or the other physical health testing device on; and/or generating data corresponding to the user's height and/or weight (e.g., in accordance with the procedure described above with respect to FIG. 8). In this regard, the user, the scale, the tape measure, and/or the other physical health testing device generate the user's height and/or weight data. In some embodiments, the scale can measure the user's weight and/or BMI and communicate the user's weight and/or BMI to the hub and/or to the software application running on the user's device. In embodiments in which the user's height and/or weight data is communicated to the hub from the scale or another physical health testing device associated with the height and/or weight physical health test, the hub can disconnect from the scale or the other physical health testing device and can communicate the user's height and/or weight data to the software application running on the user's device. In some embodiments, the hub can format the user's height and/or weight data it received from the scale or the other physical health testing device before sending the formatted user height and/or weight data to the software application. In these and other embodiments, the hub can perform one or more calculations (e.g., BMI and/or relative fat mass (RFM)) using the user's height and/or weight data, and can communicate the results of the calculations to the software application. Alternatively, the software application can perform one or more of the calculations once it receives the user's height and/or weight data. In some embodiments, the user can review all or a subset of the height, weight, BMI, and/or RFM health data on the software application (as discussed in greater detail below with respect to block 913). In these and other embodiments, the routine 900 can store all or a subset of the user's height, weight, BMI, and/or RFM data (e.g., on one or more remote servers and/or databases, and/or associated with the user's account) using the software application and/or the hub.

At block 910, the routine 900 continues when a user initiates a temperature physical health test to generate the user's temperature data. For example, the user can initiate the temperature physical health test by pressing a start button associated with the physical health test that is presented to the user on a UI of the software application. In response, the software application can instruct the hub to connect to a thermometer of the modular system. In turn, the hub can attempt to connect with the thermometer. In some embodiments, the hub can instruct the thermometer to power on before attempting to connect to the thermometer. Alternatively, the software application can request that the user perform the temperature physical health test without instructing the hub to connect to a thermometer or another physical health testing device associated with the temperature physical health test. In these and other embodiments, the software application can request the user to manually enter one or more components of his/her temperature data after performing the temperature physical health test.

In some embodiments, the software application running on the user's device can provide instructions (e.g., via one or more UIs) for performing the temperature physical health test, such as instructions for removing a thermometer from the modular system, turning the thermometer on, and/or generating temperature data corresponding to the user's internal body temperature (e.g., in accordance with the procedure described above with respect to FIG. 4). In this regard, the thermometer can measure the user's internal body temperature and communicate the user's internal body temperature to the hub and/or to the software application running on the user's device. In some embodiments, the software application instructs the user to conduct several (e.g., two or more) measurements of their internal body temperature, which can each be communicated to the hub and/or to the software application. In embodiments in which the user's temperature data is communicated to the hub from the thermometer or another physical health testing device associated with the temperature physical health test, the hub can disconnect from the thermometer or the other physical health testing device and can communicate the user's temperature data to the software application running on the user's device. In some embodiments, the hub can format the user's temperature data it received from the thermometer or the other physical health testing device before sending the formatted user temperature data to the software application. In these and other embodiments, the hub can perform one or more calculations (e.g., averaging multiple temperature measurements together to generate an official internal body temperature of the user) using the user's temperature data, and can communicate the results of the calculations to the software application. Alternatively, the software application can perform one or more of the calculations once it receives the user's temperature data. In these and other embodiments, the user can review all or a subset of the user's temperature data on the software application (as discussed in greater detail below with respect to block 913). In these and still other embodiments, the routine 900 can store all or a subset of the user's temperature data (e.g., on one or more remote servers and/or databases, and/or associated with the user's account) using the software application and/or the hub.

At block 911, the routine 900 continues when a user initiates a heart activity physical health test to generate the user's heart activity data. For example, the user can initiate the heart activity physical health test by pressing a start button associated with the physical health test that is presented to the user on a UI of the software application. In response, the software application can instruct the hub to connect to a digital stethoscope of the modular system. In turn, the hub can attempt to connect with the stethoscope. In some embodiments, the hub can instruct the stethoscope to power on before attempting to connect to the stethoscope.

In these and other embodiments, the software application running on the user's device can provide instructions (e.g., via one or more UIs) for performing the heart activity physical health test, such as instructions for removing a stethoscope from the modular system, turning the stethoscope on, and/or generating activity data corresponding to the user's heart (e.g., in accordance with the procedure described above with respect to FIGS. 6A-6C). In this regard, the stethoscope generates the user's heart activity data (e.g., an ECG and/or a PCG).

After the stethoscope has generated the user's heart activity data, the stethoscope can enable Bluetooth (or another communication means) and can connect with the hub. When the hub successfully connects with the stethoscope, the hub can notify the user device that connection was successful. After the hub connects with the stethoscope, the hub can attach to a data stream of one or more sensors of the stethoscope. In turn, the stethoscope communicates the heart activity data to the hub. Once the hub has received (e.g., a predetermined amount of) the user's heart activity data, the hub can disconnect from the stethoscope. The hub can then communicate the user's heart activity data to the software application running on the user's device. In some embodiments, the hub can format the user's heart activity data it received from the stethoscope before sending the formatted user heart activity data to the software application. In these and other embodiments, the user can review all or a subset of the user's heart activity data on the software application (as discussed in greater detail below with respect to block 913). In these and other embodiments, the routine 900 can store all or a subset of the user's heart activity data (e.g., on one or more remote servers and/or databases, and/or associated with the user's account) using the software application and/or the hub.

At block 912, the routine 900 continues when a user initiates a blood physical health test to generate the user's blood data. For example, the user can initiate the blood physical health test by pressing a start button associated with the physical health test that is presented to the user on a UI of the software application. In response, the software application can instruct the hub to connect to a glucose and/or cholesterol blood testing device of the modular system. In turn, the hub can attempt to connect with the glucose and/or cholesterol blood testing device. In some embodiments, the hub can instruct the glucose and/or cholesterol blood testing device to power on before attempting to connect to the stethoscope.

When the glucose and/or cholesterol blood testing device is powered on, the glucose and/or cholesterol blood testing device can enable Bluetooth (or another communication means) and can connect with the hub. When the hub successfully connects with the glucose and/or cholesterol blood testing device, the hub can notify the user device that connection was successful. In some embodiments, the hub can request (and the glucose and/or cholesterol blood testing device can provide) connection characteristic information (e.g., Bluetooth Low Energy characteristic information). After the hub receives the characteristic information from the glucose and/or cholesterol blood testing device, the hub can subscribe to notifications from the glucose and/or cholesterol blood testing device (e.g., relating to all or specific blood data of the user).

In these and other embodiments, the software application running on the user's device can provide instructions (e.g., via one or more UIs) for performing the blood physical health test, such as instructions for removing a glucose and/or cholesterol blood testing device from the modular system, turning the glucose and/or cholesterol blood testing device on, and/or generating blood data corresponding to the user's blood (e.g., in accordance with the procedure described above with respect to FIG. 7). In this regard, the glucose and/or cholesterol blood testing device generates blood data (e.g., HDL levels, LDL levels, total cholesterol levels, ratios of HDL to LDL, TRIG levels, lipids levels, eGLU levels, etc.).

In some embodiments, the software application can alert the user (e.g., via one or more UIs) to potential scenarios that would lead to inaccurate test results. FIG. 10H illustrates a partially schematic view of such a UI in accordance with various embodiments of the present technology, that includes an alert based on local time data the software application gathers from the user's device. In particular, the UI illustrated in FIG. 10H (a) informs the user that it is currently evening, (b) includes a recommendation that the user fast (e.g., over the evening) for at least nine hours before performing the blood physical health test (e.g., the next morning) to increase the accuracy of the results, and (c) provides the user the option to either set a reminder to conduct the blood physical health test at a later time or continue with performing the blood physical health test now.

After the glucose and/or cholesterol blood testing device conducts the blood physical health test, the glucose and/or cholesterol blood testing device can communicate the user's blood data to the hub in one or more packets of information. For example, the glucose and/or cholesterol blood testing device can send a first packet of information to the hub that includes the user's total cholesterol. In response, the hub can acknowledge receipt of the first packet of information to the glucose and/or cholesterol blood testing device. The glucose and/or cholesterol blood testing device can then send a second packet of information to the hub that includes the user's HDL cholesterol. In response the hub can acknowledge receipt of the second packet of information to the glucose and/or cholesterol blood testing device. Communication between the glucose and/or cholesterol blood testing device and the hub can continue in this manner to transmit the user's triglycerides, glucose, LDL cholesterol, total cholesterol/HDL ratio, LDL/HDL ratio, non-HDL cholesterol, and/or other blood data generated by the glucose and/or cholesterol blood testing device. The hub then communicates the user's blood data to the software application running on the user's device. In some embodiments, the hub can format the user's blood data it received from the glucose and/or cholesterol blood testing device before sending the formatted user blood data to the software application.

In some embodiments, the routine 900 can store all or a subset of the user's blood data (e.g., on one or more remote servers and/or databases, and/or associated with the user's account) using the software application and/or the hub. After the software application receives the user's blood data from the hub, the software application can instruct the hub to disconnect from the glucose and/or cholesterol blood testing device. In turn, the hub can disconnect from the glucose and/or cholesterol blood testing device and can send a disconnect successful notification to the software application. In some embodiments, the user can review all or a subset of the user's blood data on the software application (as discussed in greater detail below with respect to block 913).

At block 913, the routine 900 continues by analyzing the generated health data, generating a physical exam report associated with the user, and/or storing all or a subset of the generated report. For example, the routine 900 (e.g., the individual physical health testing devices, the hub, and/or the software application on the user's device) analyzes all or a subset of the generated health data to identify potential health concerns. In this regard, the routine 900 can compare all or a subset of the generated health data to predetermined "healthy" or "normal" ranges of data. Thus, the routine 900 can indicate in the generated physical exam report which of the physical tests generated health data within a corresponding normal or healthy range of data and which fell outside of a corresponding normal or healthy range of data. In this manner, a user or another individual can review the generated physical exam report and can identify potential health concerns or areas in which further physical health testing is required.

Results of the physical health tests and/or the subsequent analysis can be presented to the user in a physical exam report. For example, FIG. 10I is a partially schematic view of a physical exam overview UI of the software application in accordance with various embodiments of the present technology. The physical exam overview UI can provide the user a summary for one or more of the physical health tests to provide the user an overview of the results of the physical health tests conducted as part of the physical exam.

Figures 10J, 10K, 10L:
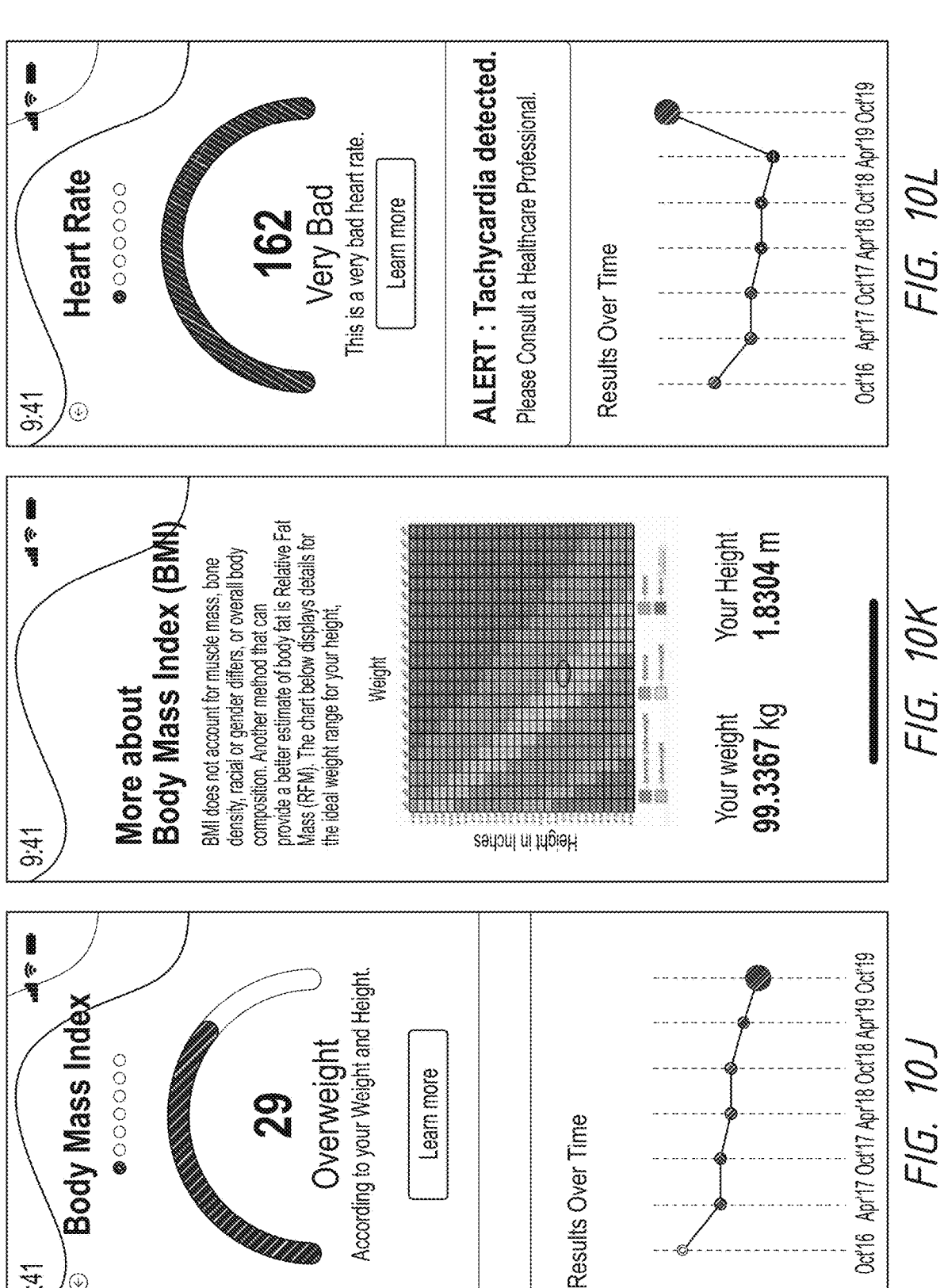

In some embodiments, the user can select a summary of a physical health test provided in the physical health overview UI to review a more detailed results summary of the corresponding physical health test. For example, FIG. 10J is a partially schematic view of a detailed BMI results summary UI of the software application generated based at least in part on a user's height and/or weight data in accordance with various embodiments of the present technology. A user can view the detailed BMI results summary UI by selecting the BMI summary provided in the physical exam overview UI (FIG. 10I). As shown in FIG. 10J, the detailed BMI results summary UI includes the user's BMI (e.g., 29 kg/m²) calculated based at least in part on the results of the height and/or weight physical health test, a graphical scale indicating the results in comparison to a predetermined "healthy" or "normal" BMI range, and a plot illustrating the user's BMI results over time (e.g., over multiple physical exams). In some embodiments, the graphical scale can be color coded (e.g., green for good or average results, orange for slightly within or slightly outside the "healthy" range, and/or red for outside of the "healthy" range to indicate a cause for concern). Here, the user's BMI suggests that the user is overweight, and the graphical scale is color coded orange to suggest that the user's BMI is either only slightly within or is slightly outside of a predetermined "healthy" BMI range.

When a user's results fall greatly outside of a corresponding predetermined "healthy" range, one or more of the detailed results summary UIs of the software application can include health alerts to highlight potential health risks and concerns for the user. For example, FIG. 10L is a partially schematic view of a detailed heart rate results summary UI of the software application in accordance with various embodiments of the present technology. As shown, the user's heart rate is 162 bpm, which falls greatly outside of the predetermined "healthy" heart rate range. As such, the scale is color coded red and the user's heart rate results are labeled as "Very Bad." The detailed heart rate results summary UI further includes an alert that is prominently displayed to attract the user's attention. In some embodiments, the alert can include a suggestion to consult a healthcare professional, suggestions for improving the results, and/or information regarding the health risks associated with the user's bad results.

In these and other embodiments, additional information can be included on one or more of the detailed results summary UIs of the software application. For example, a detailed ECG or EKG results summary UI (not shown) of the software application can include an embedded file for the user to review a data stream generated by a sensor of the ECG device. As another example, a detailed glucose results summary UI (not shown) of the software application can prompt the user for a response indicating whether or not the user fasted (e.g., for a predetermined amount of time) prior to conducting the blood physical health test.

In these and still other embodiments, one or more UIs of the software application can provide the user an explanation of the analysis underlying the results of a physical health test. For example, referring again to FIG. 10J, the detailed BMI results summary UI includes a "Learn more" button, which a user can select to review how his/her results were calculated based on the height and/or weight data generated during the height and/or weight physical health test. FIG. 10K is a partially schematic view of a BMI results explanation UI of the software application in accordance with various embodiments of the present technology, that can be presented to the user when the user selects the "Learn more" button on the detailed BMI results summary UI of FIG. 10J. As shown in FIG. 10K, the BMI results explanation UI includes the user's height and weight data generated during the height and/or weight physical health test, as well as an explanation and corresponding graph of the BMI calculation.

Figures 10M, 10N:
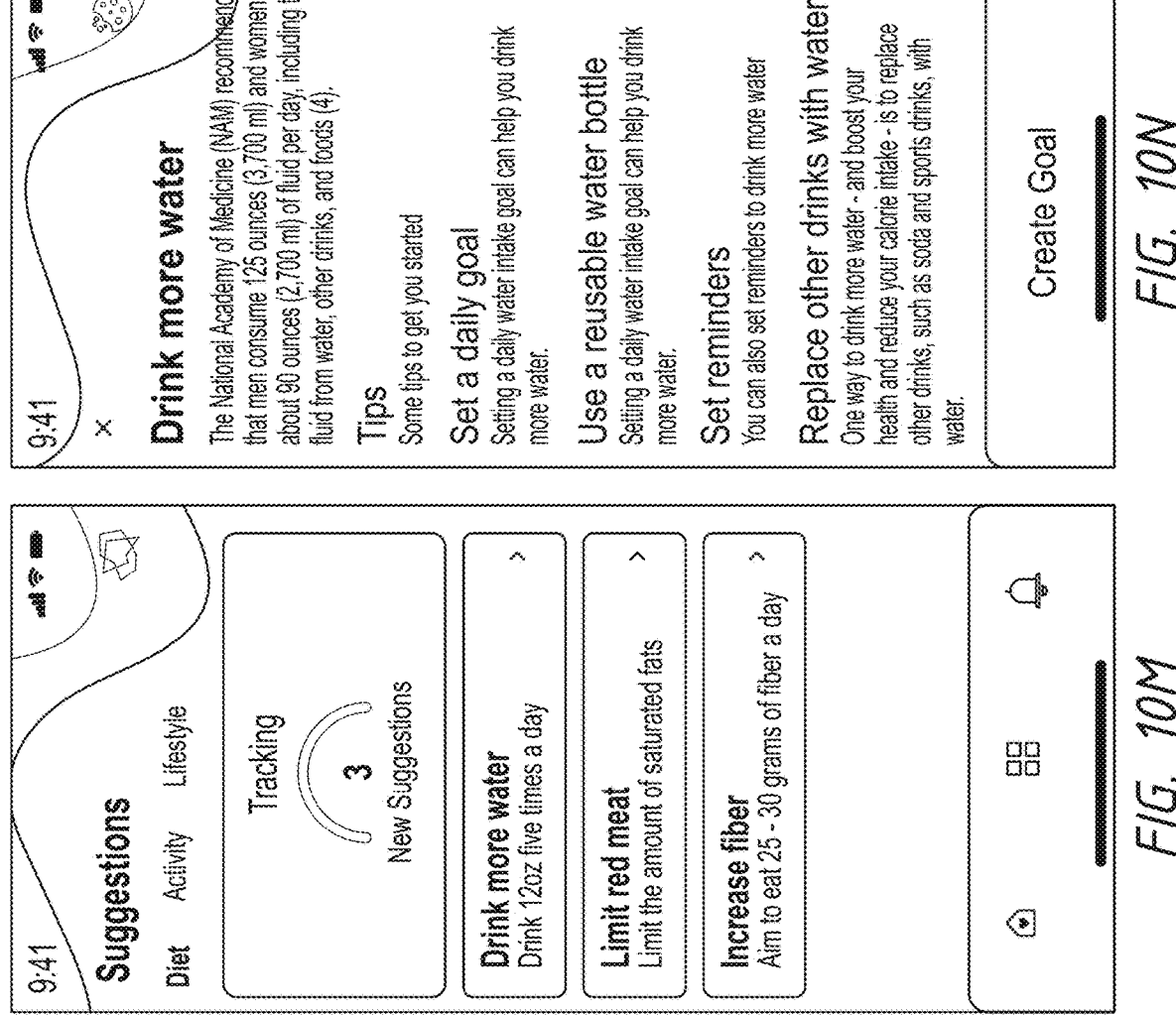

In some embodiments, the routine 900 can (e.g., via one or more UIs of the software application) provide the user tips and suggestions for improving their health, encourage the user to set goals to better his/her health, and/or allow the user to set reminders (e.g., to drink more water). The tips, suggestions, goals, and/or reminders can be based at least in part on results of individual physical health tests and/or on results of a collection of two or more physical health tests. FIGS. 10M and 10N are partially schematic views of a suggestions UI and a tips and goals UI, respectively, of the software application in accordance with various embodiments of the present technology.

In these and other embodiments, the routine 900 can recommend that a user consult a healthcare professional. As discussed above, the routine 900 can recommend that a user consult a healthcare professional in the event that generated health data falls outside of a corresponding healthy and/or normal range of data. In these and other embodiments, the routine 900 can recommend that a user consult a healthcare professional in the event that a user skips one or more steps of a physical exam and/or in the event of an error when conducting a physical health test of a physical exam. In these and still other embodiments, the routine 900 can recommend specific healthcare professionals or hospitals (e.g., healthcare professionals or hospitals in the user's geographic area, healthcare professionals specializing in a corresponding medical field, etc.).

In some embodiments, all or a subset of the generated physical exam report can be stored for future reference, analysis, and/or review. For example, the software application running on the user's device and/or the hub can send the generated physical exam report to one or more remote servers to be stored in one or more database entries of one or more databases associated with the user's account.

Additionally, or alternatively, the routine 900 can individually analyze the generated health data received from each physical health testing device of the modular system (e.g., as the health data is transmitted to the hub and/or to the software application during each physical health test, and/or at the conclusion of the entire physical exam). In these and other embodiments, the routine 900 can generate a plurality of physical test reports that can be displayed to a user (e.g., as the user conducts each physical health test or at the conclusion of the entire physical exam) and/or that can be individually stored for future reference, analysis, and/or review.

At block 914, the routine 900 continues by transmitting all or a subset of a user's generated health data to a healthcare professional. In some embodiments, the routine 900 can transmit all or a subset of a user's generated health data report to a healthcare professional at the direction of the user (e.g., via the software application). For example, the routine 900 can transmit all or a subset of the physical exam report generated at block 913. In these and other embodiments, the routine 900 can generate a (e.g., permanent or temporary) code corresponding to the user's account and/or a notification indicating that the user has generated new health data, and the routine 900 can send the code and/or the notification to a healthcare professional. In turn, the healthcare professional can retrieve all or a subset of the health report generated at block 913 using the generated code and/or by responding to the notification (e.g., by logging into an application, website, and/or database associated with the modular system and/or entering the code). In these and still other embodiments, the routine 900 can automatically send all or a subset of a user's generated health data to a healthcare professional (e.g., to update the user's medical records) in accordance with the user's prior approval to automatically share the generated health data with the healthcare professional.

At block 915, the routine 900 concludes by returning the modular physical health testing system to a supplier or vendor. For example, a user can ship the modular system back to a supplier or vendor (e.g., using a prepaid shipping label included with the modular system). In these and other embodiments, a user can return the modular system by returning the modular system to a location (e.g., a pharmacy or hospital) from which he/she checked-out the modular system. In some embodiments, the routine 900 can return to block 901 after the routine 900 returns the modular system to the supplier or vendor.

Although the steps of routine 900 are discussed and illustrated in a particular order, the routine 900 is not so limited. In other embodiments, the routine 900 can perform steps in a different order. In these and other embodiments, any of the steps of the routine 900 can be performed before, during, and/or after any of the other steps of the routine 900. Furthermore, a person of ordinary skill in the art will readily recognize that the routine 900 can be altered and still remain within these and other embodiments of the present technology. For example, steps of the routine 900 in some embodiments can be skipped (e.g., by a user via the software application), such as when an error occurs with a physical health test of the physical exam or for other reasons (e.g., the user experiences needle anxiety when conducting a blood test). Moreover, one or more steps of the routine 900 illustrated in FIG. 9 can be omitted and/or repeated in some embodiments.

Although not shown so as to avoid unnecessarily obscuring the description of embodiments of the technology, any of the forgoing systems and methods described above in FIGS. 1-10N can include and/or be performed by one or more computing devices configured to direct and/or arrange components of the systems and/or to receive, arrange, store, analyze, and/or otherwise process data received, for example, from the machine and/or other components of the systems. As such, such computing devices include the necessary hardware and corresponding computer-executable instructions to perform these tasks. More specifically, computing devices configured in accordance with an embodiment of the present technology can include a processor, a storage device, input/output devices, one or more sensors, and/or any other suitable subsystems and/or components (e.g., displays, speakers, communication modules, etc.). The storage device can include a set of circuits or a network of storage components configured to retain information and provide access to the retained information. For example, the storage device can include volatile and/or non-volatile memory. As a more specific example, the storage device can include random access memory (RAM), magnetic disks or tapes, and/or flash memory.

The computing devices can also include computer readable media (e.g., the storage device, disk drives, and/or other storage media, excluding only a transitory, propagating signal per se) including computer-executable instructions stored thereon that, when executed by the processor and/or computing device, cause the systems to perform physical health testing procedures as described in detail above with reference to FIGS. 1-10N. Moreover, the processor can be configured for performing or otherwise controlling steps, calculations, analysis, and any other functions associated with the methods described herein.

In some embodiments, the storage device can store one or more databases used to store data collected by the systems as well as data used to direct and/or adjust components of the systems. In one embodiment, for example, a database is an HTML file designed by the assignee of the present disclosure. In other embodiments, however, data is stored in other types of databases or data files.

One of ordinary skill in the art will understand that various components of the systems (e.g., the computing device) can be further divided into subcomponents, or that various components and functions of the systems may be combined and integrated. In addition, these components can communicate via wired and/or wireless communication, as well as by information contained in the storage media.

B. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order above, alternative embodiments may perform steps in a different order. Furthermore, the various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any material incorporated herein by reference conflicts with the present disclosure, the present disclosure controls. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Furthermore, as used herein, the phrase "and/or" as in "A and/or B" refers to A alone, B alone, and both A and B. Additionally, the terms "comprising," "including," "having," and "with" are used throughout to mean including at least the recited feature(s) such that any greater number of the same features and/or additional types of other features are not precluded.

From the foregoing, it will also be appreciated that various modifications may be made without deviating from the disclosure or the technology. For example, one of ordinary skill in the art will understand that various components of the technology can be further divided into subcomponents, or that various components and functions of the technology may be combined and integrated. In addition, certain aspects of the technology described in the context of particular embodiments may also be combined or eliminated in other embodiments. Furthermore, although advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of operating a physical health testing system using a software application running on a user device, the method comprising:

instructing the user device to communicatively connect to a communications hub of the physical health testing system;

while the user device is communicatively connected to the communications hub, subscribing to notifications from the communications hub, wherein the notifications correspond to multiple physical health testing devices that are each communicatively couplable to the communications hub;

receiving instructions to initiate a first physical health test and a second physical health test;

in response to receiving the instructions to initiate the first and second physical health tests, instructing the communications hub to communicatively connect to the multiple physical health testing devices, wherein the a first physical health testing device of the multiple physical health testing devices is configured to execute at least a portion of the first physical health test and wherein a second physical health testing device of the multiple physical health testing devices is configured to execute at least a portion of the second physical health test;

and receiving, from the communications hub, health data of a user in one or more notifications, wherein the health data corresponds to (a) a first data obtained via the first physical health test and (b) a second data obtained via the second physical health test, and causing display of, on a user interface of the user device, (a) a first visual feedback of the first data and (b) a second visual feedback of the second data, wherein the first and second visual feedback are determined based on (a) whether the first data is within a first range or (b) whether the second data is within a second range, respectively;

wherein the first and second visual feedback include a plurality of fillable arcuate meter icons which are simultaneously displayed to the user, wherein each one of the arcuate icons represents a health goal specific to the first data and the health data, wherein under each arcuate icon there is displayed a text string detailing either of a treatment suggestion or a health status summary.

2. The method of claim 1, wherein instructing the user device to communicatively connect to the communications hub comprises instructing the user device to wirelessly connect to the communications hub.

3. The method of claim 1, wherein receiving the instructions to initiate at least one of the first physical health test or the second physical health test comprises receiving user input via a user interface displayed on the user device.

4. The method of claim 1, further comprising, before or during at least one of the first physical health test or the second physical health test, instructing the user device to display instructions for performing the first or second physical health test.

5. The method of claim 1, further comprising, after instructing the communications hub to communicatively connect to the multiple physical health testing devices and before receiving the health data of the user from the communications hub, receiving a notification from the communications hub indicating that the communications hub was successfully able to communicatively connect to the multiple physical health testing devices.

6. The method of claim 1, further comprising causing the user device to remain communicatively connected to the communications hub until at least one of the first physical health test or the second physical health test is complete.

7. The method of claim 1, further comprising:

after instructing the communications hub to communicatively connect to the first physical health testing device, instructing the user device to communicatively disconnect from the communications hub; and before receiving the health data of the user, instructing the user device to communicatively reconnect to the communications hub.

8. The method of claim 1, further comprising causing the user device to communicatively connect intermittently to the communications hub throughout a physical health exam that includes at least one of the first physical health test or the second physical health test.

9. The method of claim 1, further comprising receiving user input via the user interface of the user device, wherein the user input includes (i) instructions for stopping at least one of the first physical health test or the second physical health test, (ii) skipping at least one of the first physical health test or the second physical health test, or (iii) a combination thereof.

10. The method of claim 1, further comprising instructing the user device to display an indication, wherein the indication (i) notifies the user that the health data is currently being collected by the multiple physical health testing devices, (ii) notifies the user of a time remaining before the multiple physical health testing devices finishes collecting the health data, or (iii) a combination thereof.

11. The method of claim 1, further comprising instructing the user device to display, on the user interface, (i) at least a portion of the health data, (ii) results of a comparison of the health data to corresponding healthy physical health data, or (iii) a combination thereof.

12. The method of claim 1, further comprising generating a physical exam report based at least in part on the health data, instructing the user device to display at least a portion of the physical exam report, or a combination thereof.

13. The method of claim 1, further comprising instructing the user device to transmit at least a portion of the health data to a remote database or a remote server.

14. The method of claim 1, wherein the method further comprises:

receiving instructions to initiate a third physical health test;

in response to receiving the instructions to initiate the third physical health test, instructing the communications hub to communicatively connect to a third physical health testing device of the physical health testing devices, wherein the third physical health testing device is different from the first and second physical health testing devices and is configured to execute at least a portion of the third physical health test; and receiving, from the communications hub, second health data of the user in one or more second notifications, wherein the second health data corresponds to the third physical health test.

15. The method of claim 1, wherein:

instructing the communications hub to communicatively connect to the first physical health testing device of the multiple physical health testing devices includes instructing the communications hub to communicatively connect to a blood pressure monitor, an electrocardiogram device, a stethoscope, or a blood testing device; and instructing the communications hub to communicatively connect to the second physical health testing device of the multiple physical health testing devices includes instructing the communications hub to communicatively connect to the blood pressure monitor, the electrocardiogram device, the stethoscope, or the blood testing device.

16. The method of claim 1, wherein the multiple physical health testing devices comprise a blood testing device, and wherein the method further comprises instructing the user device to display a recommendation that the user fast for a period of time before conducting the first physical health test.

17. The method of claim 16, further comprising:

gathering time data corresponding to a local time of the user; and instructing the user device to display the recommendation based at least in part on the time data.

18. The method of claim 16, further comprising:

receiving instructions to set a reminder to conduct at least one of the first physical health test or the second physical health test at a later time; and reminding the user to conduct the first or second physical health test at the later time.

19. The method of claim 1, wherein the first and second visual feedback are each displayed in accordance with a first or second set of display attributes, respectively, and wherein the first and second sets of display attributes are each determined based on (a) whether the first data is within the first range or (b) whether the second data is within the second range, respectively.

20. The method of claim 19, wherein the first and second sets of display attributes are each associated with one or more of a color, an icon, an annotation, or a recommendation of the first data or the second data, respectively.

21. The method of claim 1, wherein causing display of the first visual feedback of the first data and the second visual feedback of the second data comprises:

assessing, using the communications hub, the first data and the second data to identify (a) a first classification of the first data and (b) a second classification of the second data based on (a) whether the first data is within the first range and (b) whether the second data is within the second range, wherein the first and second visual feedback correspond to the first classification of the first data and the second classification of the second data, respectively.

* * * * *